(12) United States Patent
Fuchs et al.

(10) Patent No.: US 7,351,538 B2
(45) Date of Patent: Apr. 1, 2008

(54) SYSTEMS AND METHODS FOR DETECTING AND ANALYZING POLYMERS

(75) Inventors: Martin Fuchs, Uxbridge, MA (US); John Harris, Foxborough, MA (US); Ray Meyers, Wakefield, MA (US)

(73) Assignee: U.S. Genomics, Woburn, MA (US)

( * ) Notice: Subject to any disclaimer, the term of this patent is extended or adjusted under 35 U.S.C. 154(b) by 0 days.

(21) Appl. No.: 11/210,155

(22) Filed: Aug. 23, 2005

(65) Prior Publication Data

US 2006/0078915 A1  Apr. 13, 2006

Related U.S. Application Data

(60) Provisional application No. 60/603,760, filed on Aug. 23, 2004.

(51) Int. Cl.
*C12Q 1/68* (2006.01)
*C12M 1/00* (2006.01)
*C07H 21/02* (2006.01)
*C07H 21/04* (2006.01)

(52) U.S. Cl. ...................... 435/6; 435/283.1; 536/23.1; 536/24.3

(58) Field of Classification Search .................... 435/6; 536/23.1, 24.3; 356/318, 417
See application file for complete search history.

(56) References Cited

U.S. PATENT DOCUMENTS

| | | | |
|---|---|---|---|
| 4,573,796 A | 3/1986 | Martin et al. | |
| 4,833,332 A | 5/1989 | Robertson, Jr. et al. | |
| 5,270,214 A | 12/1993 | Sessler et al. | |
| 5,356,776 A | 10/1994 | Kambara et al. | |
| 5,707,797 A | 1/1998 | Windle | |
| 5,784,157 A | 7/1998 | Gorfinkel et al. | |
| 6,038,023 A | 3/2000 | Carlson et al. | |
| 6,139,800 A | 10/2000 | Chandler | |
| 6,210,896 B1 | 4/2001 | Chan | |
| 6,210,973 B1 | 4/2001 | Pettit | |
| 6,245,507 B1 | 6/2001 | Bogdanov | |
| 6,255,083 B1 | 7/2001 | Williams | |
| 6,263,286 B1 | 7/2001 | Gilmanshin et al. | |
| 6,306,607 B2 | 10/2001 | Williams | |
| 6,355,420 B1 | 3/2002 | Chan | |
| 6,403,311 B1 | 6/2002 | Chan | |
| 6,635,163 B1 | 10/2003 | Han et al. | |
| 6,696,022 B1 | 2/2004 | Chan et al. | |
| 6,762,059 B2 | 7/2004 | Chan et al. | |
| 6,772,070 B2 | 8/2004 | Gilmanshin et al. | |
| 6,790,671 B1 | 9/2004 | Austin et al. | |
| 6,927,065 B2 | 8/2005 | Chan et al. | |
| 2002/0110818 A1 | 8/2002 | Chan | |
| 2002/0119455 A1 | 8/2002 | Chan | |
| 2002/0187508 A1 | 12/2002 | Wong | |
| 2002/0197639 A1 | 12/2002 | Shia et al. | |
| 2003/0058440 A1* | 3/2003 | Scott et al. | .................. 356/318 |
| 2003/0059822 A1 | 3/2003 | Chan et al. | |
| 2003/0215864 A1 | 11/2003 | Gilmanshin et al. | |
| 2003/0235854 A1 | 12/2003 | Chan | |
| 2004/0009612 A1 | 1/2004 | Zhao et al. | |
| 2004/0053399 A1 | 3/2004 | Gilmanshin | |
| 2004/0166025 A1 | 8/2004 | Chan et al. | |
| 2004/0214211 A1 | 10/2004 | Gilmanshin et al. | |
| 2004/0235014 A1 | 11/2004 | Nadel et al. | |
| 2005/0042665 A1 | 2/2005 | Gilmanshin | |
| 2005/0112595 A1 | 5/2005 | Zhao et al. | |
| 2005/0112606 A1 | 5/2005 | Fuchs et al. | |
| 2005/0112620 A1 | 5/2005 | Chan | |
| 2005/0112671 A1 | 5/2005 | Maletta et al. | |
| 2005/0123944 A1 | 6/2005 | Neely et al. | |
| 2005/0123974 A1 | 6/2005 | Gilmanshin et al. | |
| 2005/0142595 A1 | 6/2005 | Maletta et al. | |
| 2005/0153354 A1 | 7/2005 | Gilmanshin et al. | |
| 2005/0196790 A1 | 9/2005 | Rooke et al. | |
| 2005/0221408 A1 | 10/2005 | Nalefski et al. | |

(Continued)

FOREIGN PATENT DOCUMENTS

WO    WO 98/10097 A2    3/1998

(Continued)

OTHER PUBLICATIONS

[No Author Listed] "Discrete-Layer Notch and Rugate Notch Filters." Barr Associates, Inc. Online. http://www.barrassociates.com/opticalfilters.php?type=rugate. 3 Pages. Printed Mar. 28, 2006.

(Continued)

*Primary Examiner*—Ethan Whisenant
(74) *Attorney, Agent, or Firm*—Wolf, Greenfield & Sacks, P.C.

(57) ABSTRACT

A detection system and methods for improving the ability of the detection system to recognize labels that are disposed on a polymer. Embodiments of the invention include schemes for selecting emitters and labels used within the system in a manner that allows an increase in the number of distinct labels that can be used together in a system. In other embodiments, the detection system and methods are directed to identifying portions of a detection signal that may be associated with extra labels residing within a detection zone. In other embodiments, the detection system and methods relate to using wide field imaging detectors while reducing out of focus noise contributions to detection signals of the system. Still, other embodiments relate to the use of linear array detectors to detect labels.

23 Claims, 18 Drawing Sheets

U.S. PATENT DOCUMENTS

| | | |
|---|---|---|
| 2006/0134679 A1 | 6/2006 | Larson et al. |
| 2006/0160209 A1 | 7/2006 | Larson et al. |
| 2006/0160231 A1 | 7/2006 | Nadel et al. |
| 2006/0204978 A1 | 9/2006 | Nilsen et al. |

FOREIGN PATENT DOCUMENTS

| | | |
|---|---|---|
| WO | WO 00/09757 A1 | 2/2000 |
| WO | WO 2004/077692 A1 | 9/2004 |

OTHER PUBLICATIONS

Boone et al., Plastic advances microfluidic devices. Anal. Chem. Feb. 1, 2002;74(3):78A-86A.

Castro et al., Single-Molecule Electrophoresis Applications to Biomolecular Detection. SPIE. 1995; 2396:79-85.

Dörre et al., Techniques for single molecule sequencing. Bioimaging. 1997;5:139-52.

Ekstrøm et al., Two-point fluorescence detection and automated fraction collection applied to constant denaturant capillary electrophoresis. Biotechniques. Sep. 2000;29(3):582-4, 586-9.

Radcliff et al., Basics of flow cytometry. Methods Mol Biol. 1998;91:1-24.

Shortreed et al., High-throughput single-molecule DNA screening based on electrophoresis. Anal Chem. Jul. 1, 2000;72(13):2879-85.

Thomann et al., Automatic fluorescent tag detection in 3D with super-resolution: application to the analysis of chromosome movement. J Microsc. Oct. 2002;208(Pt 1):49-64.

Cova et al., Evolution and prospects for single-photon avalanche diodes and quenching circuits. J Mod Opt. Jun.-Jul. 2004;51(9-10):1267-88.

Nie et al., Probing individual molecules with confocal fluorescence microscopy. Science. Nov. 11, 1994;266(5187):1018-21.

Shera et al., Detection of single fluorescent molecules. Chem Phys Letts. 1990; 174(6): 553-7.

* cited by examiner

SYSTEMS AND METHODS FOR DETECTING AND ANALYZING POLYMERS

RELATED APPLICATIONS

This application is a non-provisional application of and claims priority to U.S. Provisional Application No. 60/603,760, filed Aug. 23, 2004.

FIELD OF THE INVENTION

The present invention relates generally to systems and methods for detecting and analyzing the structures of polymers, and more particularly to systems and methods for improving the detection of labels disposed on polymers, such as DNA or RNA.

BACKGROUND OF THE INVENTION

Polymer detection and analysis systems and their associated methods have been used to detect and analyze polymers for many years. Generally, such systems involve a sample, such as a polymer, labeled with a known probe that will bind to the polymer in a particular manner. The polymer is placed in a detection zone of the system where an emitter, such as a laser, is used to excite the label on the probe bound to the polymer. The label then emits an emission signal that is seen by a detector in the system as a portion of a detection signal. The characteristics of the emission signal relative to the sample, the excitation signal, the surroundings, and/or other characteristics are then used by the system to analyze the polymer structure.

Detection systems often have difficulty distinguishing emission signals from noise and/or disturbances within the system. Such noise and/or disturbances may come from any number of sources. By way of example, the excitation signal, the detection zone, hardware of the system, the sample itself, impurities within the sample, the solution in which the sample resides, and other emission signals from the same or other polymers may be the source of such noise or disturbances to a particular emission signal. Noise in these systems may reduce the quality of the detection and analysis that can be accomplished.

Labeling

Many technologies relating to genomic sequencing and analysis require site-specific labeling of nucleic acids. Most site-specific labeling is carried out using nucleic acid based probes that hybridize to their complementary sequences within a target molecule (e.g., a nucleic acid). The specificity of these probes will vary, however, depending upon their length, their sequence, the hybridization conditions, and the like. Moreover, because these probes are usually labeled with a detectable label such as a fluorophore or a radioactive label, they are expensive to synthesize. The ability to increase the specificity of these probes, and at the same time, use less of them would make labeling reactions more efficient and less expensive to run.

SUMMARY OF THE INVENTION

The systems and methods of the present invention are directed to improving the ability of a detection system to recognize labels that are disposed on polymers. Frequently, these polymers include DNA or RNA, that are being detected and analyzed by a detection system.

In one embodiment a detection system for analyzing a polymer having three or more distinct fluorophores is disclosed. Each fluorophore has an excitation wavelength and a corresponding emission bandwidth. The detection system comprises a polymer interrogation zone constructed and arranged to accept the polymer and at least three different emitters, each of the emitters constructed and arranged to emit an excitation signal substantially at an excitation wavelength of a corresponding one of the at least three fluorophores such that each fluorophore emits a distinct emission signal within its respective emission bandwidth and each distinct emission signal has an emission maximum separated by at least 60 nm from any other of the emission maximums. The detection system also comprises a detector constructed and arranged to distinctly detect the emission signal from each of the at least three fluorophores.

In another embodiment, a detection system for analyzing a polymer having three or more distinct fluorophores is disclosed. Each fluorophore has an excitation wavelength and a corresponding emission bandwidth. The detection system comprises a polymer interrogation zone constructed and arranged to accept the polymer and at least three different emitters, each of the emitters constructed and arranged to emit an emission signal substantially at an excitation wavelength of a corresponding one of the at least three fluorophores such that each fluorophore emits a distinct emission signal within its respective emission bandwidth that does not overlap any other of the distinct emission signals at normalized intensities above 70%. The detection system also comprises a detector constructed and arranged to detect the distinct emission signal from each of the at least three fluorophores.

In a related embodiment, the detection system comprises each of the emitters constructed and arranged to emit its excitation signal within the excitation wavelength of one of the at least three distinct fluorophores such that each fluorophore emits a distinct emission signal within its respective emission bandwidth that does not overlap any other of the distinct emission signal at normalized intensities above 50%.

In another related embodiment, the detection system comprises each of the emitters constructed and arranged to emit its excitation signal within the excitation wavelength of one of the at least three distinct fluorophores such that each fluorophore emits a distinct emission signal within its respective emission bandwidth that does not overlap any other of the distinct emission signal at normalized intensities above 30%.

In another embodiment, a detection system for analyzing a polymer having three or more distinct fluorophores is disclosed. Each fluorophore has an excitation wavelength and a corresponding emission bandwidth. The detection system comprises a polymer interrogation zone constructed and arranged to accept the polymer. The detection system also comprises at least three different emitters, each of the emitters constructed and arranged to emit an excitation signal substantially at an excitation wavelength of a corresponding one of the at least three fluorophores such that each fluorophore emits a distinct emission signal within its respective emission bandwidth, each of the at least three emitters and corresponding at least three fluorophores selected from a group consisting of: an emitter emitting an excitation signal substantially at a wavelength of 488 nm and a corresponding fluorophore having an emission maximum substantially located at 512 nm, an emitter emitting an excitation signal substantially at a wavelength of 532 nm and a corresponding fluorophore having an emission maximum substantially located at 575 nm, an emitter emitting an excitation signal substantially at a wavelength of 633 nm and a corresponding fluorophore having an emission maximum substantially located at 665 nm, and an emitter emitting an excitation signal substantially at a wavelength of 750 nm and a corresponding fluorophore having an emission maximum substantially located at 775 nm or 806 nm. The detection system further comprises a detector constructed and arranged to detect the distinct emission signal from each of the at least three fluorophores.

Another embodiment of the invention includes a method of detecting emissions of three or more distinct fluorophores bound to a polymer. The method comprises selecting three or more fluorophores, each of the fluorophores characterized by an excitation wavelength and a corresponding emission bandwidth, the emission bandwidth of each of the fluorophores not overlapping the emission bandwidth of any other of the fluorophores at normalized intensities above 70%. The method also comprises attaching the three or more fluorophores to the polymer in a sequence specific manner and illuminating each of the fluorophores with an excitation signal within the excitation wavelength of the corresponding fluorophores, thereby causing each of the fluorophores to emit an emission signal within the emission bandwidth of the fluorophore. The method also includes detecting and analyzing the emission signal of each of the fluorophores.

In a related method, the selecting three or more fluorophores comprises selecting three or more fluorophores, each of the fluorophores characterized by an excitation bandwidth and a corresponding emission bandwidth, the emission bandwidth of each of the fluorophores not overlapping the emission bandwidth of any other of the fluorophores at normalized intensities above 50%.

In another related method, selecting three or more fluorophores comprises selecting three or more fluorophores, each of the fluorophores characterized by an excitation bandwidth and a corresponding emission bandwidth, the emission bandwidth of each of the fluorophores not overlapping the emission bandwidth of any other of the fluorophores at normalized intensities above 30%.

Yet another method is disclosed for analyzing a polymer. The method comprises selecting at least three distinct fluorophores and at least three different excitation signals each emitted from a corresponding emitter, each of the at least three fluorophores having an excitation wavelength and a corresponding emission bandwidth, each of the excitation signals having an excitation wavelength of a corresponding one of the at least three fluorophores such that each fluorophore emits a distinct emission signal having an emission maximum within its respective emission bandwidth, each of the at least three excitation signals and corresponding at least three fluorophores selected from a group consisting of: an excitation signal having a wavelength of 488 nm and a corresponding fluorophore having an emission maximum substantially located at 512 nm, an excitation signal having a wavelength of 532 nm and a corresponding fluorophore having an emission maximum substantially located at 575 nm, an excitation signal having a wavelength of 633 nm and a corresponding fluorophore having an emission maximum substantially located at 665 nm, and an excitation signal having a wavelength of 750 nm and a corresponding fluorophore having an emission maximum substantially located at 775 nm or 806 nm. The method also comprises binding the at least three fluorophores to a polymer in a sequence specific manner and illuminating each of the fluorophores with the corresponding emitter. Detecting and analyzing the emission signal of each of the fluorophores are also included in the method.

In some related embodiments the at least three fluorophores are selected from the group consisting of: Bodipy FL fluorophore, Tamra fluorophore, Alexa 647 fluorophore, Alexa 750 fluorophore, and IR 38 fluorophore.

In some embodiments, the detector comprises a plurality of detectors. In one embodiment, the plurality of detectors comprises a plurality of avalanche photon detectors.

Some embodiments also comprise a plurality of dichroic mirrors constructed and arranged to direct each of the distinct emission signals into one of the plurality of detectors. Still, some embodiments comprise a polychroic mirror adapted to prevent excitation signals emitted from the at least three different emitters from reaching the detector. Embodiments may also comprise a bandpass filter for removing noise from each of the emission signals.

Still, in some embodiments the at least three different emitters comprise four different emitters and the at least three different fluorophores comprise four different fluorophores.

The emitters comprise lasers in some of the disclosed embodiments. Still in some embodiments, the excitation signals comprise coherent light. The polymer, in some embodiments, is a single polymer.

In an embodiment, a detection system for analyzing a polymer is disclosed. The detection system comprises a first detection zone disposed in a first area of a microchannel and adapted to detect a polymer having first and second polymer portions to create a first detection signal when the polymer is in the first zone and a second detection zone disposed in a second area of the microchannel that is different from the first area, the second detection zone adapted to detect the second polymer portion to create a second detection signal when the second portion is in the second area. The embodiment also comprises a data processor adapted to comparing the first and second detection signals and identify components that are not common to both the first and second detection signals.

Also disclosed is a method of analyzing a polymer in a detection system. The method comprises passing a plurality of polymers comprising a first polymer portion and a second polymer portion through a first detection zone to create a first detection signal, the first detection zone disposed in a first area of the microchannel and passing the second portion of polymers through a second detection zone to create a second detection signal, the second detection zone disposed in a second area of the microchannel. The method also comprises identifying components of the first detection signal that are associated with the second polymer portion by comparing the first detection signal with the second detection signal and detecting components of the first detection signal associated with the second polymer portion to analyze the polymers.

In some embodiments, the second detection zone is substantially overlapped with the first detection zone. Still, in some embodiments the first detection zone and the second detection zone are substantially circular. The second detection zone is concentric with the first detection zone and the second detection zone is disposed entirely within the first detection zone.

In some embodiments, the first detection zone has a diameter of approximately 1.00 microns and the second detection zone has a diameter of approximately 0.50 microns.

In some illustrative embodiments the system further comprises an emitter for illuminating the first detection zone, the emitter adopted to emit on excitation signal having low intensity components and high intensity components.

In some embodiments the first detection zone covers areas having both low and high intensity components of the excitation signal while the second detection zone covers areas having substantially only high intensity components of the excitation signal.

Still, in some embodiments the data processor is adapted to remove at least some portions of emission signals associated with the first detection zone of the low intensity components of the excitation signal from the first detection signal to improve the identification of the second polymer portion by the first detection signal.

In some aspects of some embodiments, the first and second detection zones are adapted to detect a polymer or polymer portion having a label that fluoresces. Still, in some embodiments the polymer comprises a plurality of polymers, each of the first and second polymer portions comprising separate polymers.

Related embodiments further comprise modifying the first detection signal by removing components of the first detection signal that are not also associated only with the second detection signal to improve the identification of the second polymer portion by the first detection signal.

In some of the embodiments, passing the plurality of polymers comprises moving both the first detection zone and the second detection zone relative to the first and second portion of polymers. Still, in some embodiments, passing the plurality of polymers comprises flowing the plurality of polymers within a fluid through the microchannel. In some of the embodiments, passing the second portion of polymers through the second detection zone comprises passing the second portion of polymers through the second detection zone that is completely overlapped with the first detection zone.

In an illustrative embodiment, passing a plurality of polymers through the first detection zone comprises passing a plurality of polymers through the first detection zone defined by a high intensity region and a low intensity region and passing the second portion of polymers through the second detection zone comprises passing the second portion of the polymer through the second detection zone that does not include the low intensity region.

In one illustrative embodiment, identifying the components of the first detection signal that are associated with the second polymer portion comprises comparing a histogram of signal intensities for the first detection signal with a histogram of signal intensities for the second detection signal.

In another illustrative embodiment modifying the first detection signal comprises removing low intensity components from the first detection signal that are not also present in second detection signal.

In one illustrative embodiment, passing a plurality of polymers through a first detection zone comprises passing a plurality of polymers through a circular detection zone having a diameter of approximately 1.00 microns and passing the second portion of polymers through a second detection zone comprises passing a plurality of polymers through a second circular detection zone having a diameter of approximately 0.50 microns and that is substantially centered within the first detection zone.

In one illustrative embodiment, a detection system is disclosed to detect a label disposed on a polymer. The detection system comprises a channel constructed and arranged to receive the polymer carried in a carrier fluid. The channel has a sample area defined by upper and lower channel surfaces separated from one another by a channel height less than about 0.500 microns. Also disclosed is an emitter constructed and arranged to illuminate the sample area with an excitation signal to excite the label in the sample area, thereby causing the label to emit an emission signal and a detector constructed and arranged to detect a detection signal from a detection zone disposed within the sample area, the detection signal including the emission signal, the detection zone being disposed at least partially within the sample area.

In one of the embodiments, channel height is less than about 0.100 microns and in some embodiments, channel height is less than about 0.050 microns. In the detection system of some embodiments, the sample area of the channel has a channel width less than about 250 microns. The detection system of some embodiments, includes the sample area constructed and arranged to receive not more than 50 nanoliters/second of carrier fluid.

The emitter is a laser in some of these embodiments. In particular, in some embodiments of the detection system, wherein the laser is one or more lasers selected from the group consisting of: a laser emitting light substantially at a wavelength of 488 nm, a laser emitting light substantially at a wavelength of 532 nm, a laser emitting light substantially at a wavelength of 633 nm, and a laser emitting light substantially at a wavelength of 750 nm.

In some embodiments of the detection system, the label is a fluorophore. Still, in some embodiments, the fluorophore is one or more fluorophores selected from the group consisting of: a fluorophore having an emission maximum substantially located at 512 nm, a fluorophore having an emission maximum substantially located at 575 nm, a fluorophore having an emission maximum substantially located at 665 mm, a fluorophore having an emission maximum substantially located at 775 nm, and a fluorophore having an emission maximum substantially located at 806 nm.

It is also disclosed that in some embodiments of the detection system, the upper or lower surface of the channel are adapted to transmit the excitation signal or detection signal without contributing noise. The material is fused silica in some of these embodiments.

Additionally, in some embodiments of the detection system, the detector comprises a CCD array. In some of these embodiments, the CCD array comprises a linear CCD array.

In another embodiment, a method to detect a label disposed on a polymer is disclosed. The method comprises providing a carrier fluid containing the polymer and providing a channel constructed and arranged to receive the carrier fluid. The channel has a sample area defined by upper and lower channel surfaces separated from one another by a channel height less than about 0.500 microns. Also disclosed is exciting the label with an excitation signal, causing the label to emit an emission signal and detecting the emission signal.

In yet another embodiment, a detection system is disclosed to detect a label disposed on a polymer. The detection system comprises a channel adapted to allow a carrier fluid containing a polymer to pass in a flow direction through the channel and through a detection zone within the channel. Also disclosed is an emitter constructed and arranged to emit an excitation signal as a sheet of light into the detection zone and a detector constructed and arranged to detect a detection signal emanating from the detection zone from a direction substantially orthogonal to the sheet of light. The detection signal includes an emission signal from the label when the label is present in the zone and excited by the excitation signal.

In some embodiments of the detection system, the detector has a focal plane lying substantially within the sheet of light. Still, according to some embodiments, the detection system further comprises a cylindrical lens adapted to form the sheet of light.

Also disclosed are some embodiments of the detection system where the sheet of light is disposed in the channel such that substantially all of the carrier fluid passes through the sheet of light when passing through the channel.

In still another embodiment, a method for detecting a label on a polymer having the label. The method comprises providing a carrier fluid containing the polymer and providing a channel having a detection zone located within the channels. The method also comprises flowing the carrier fluid through the channel in a flow direction and through a detection zone in the channel, and emitting an excitation signal as a sheet of light into the detection zone. Also disclosed is detecting, with a detector, an emission signal from the label when the label is present in the zone and excited by the excitation signal. The detector is located in a direction substantially orthogonal to the sheet of light.

In yet another embodiment, a detection system for detecting a first and second distinct labels on a polymer is disclosed. The detection system comprises a detection zone adapted to receive the polymer for detection and an emitter for exciting each of the first and second distinct labels on the polymer when in the detection zone, causing each of the first and second distinct labels to emit a first and second emission signal, respectively. The system also comprises a mirror adapted to substantially separate the first and second emission signals from one another and a wide field detector adapted to receive the first and second emission signals on spatially separate portions of a detection surface.

Also disclosed is a method of detecting a first and a second distinct label on a polymer. The method comprises providing a detection zone and placing the polymer and the label into the detection zone. The method also comprises emitting an excitation signal for exciting the first and second distinct labels, causing the first and second labels to emit a first and second emission signal, respectively. Also discloses is substantially separating the first and second emission signals from one another and detecting the first and second emission signals on a spatially separated portions of a detector.

In another embodiment, a detection system is disclosed for analyzing a polymer having a label. The detection system comprises a channel adapted to provide a carrier fluid containing a polymer through the channel in a flow direction and a detection zone lying within the channel. The detection zone comprises a substantially linear array, the array arranged in a direction substantially orthogonal to the flow direction. The system also comprises an emitter constructed and arranged to emit an excitation signal into the detection zone. The excitation signal comprises a sheet of light extending into the detection zone. Also discloses is a detector constructed and arranged to detect an emission signal from the label when the label is present in the detection zone and excited by the excitation signal. In some embodiments of the detection system, the detector is a linear CCD array.

In some of these embodiments, the polymer is a nucleic acid. Also, in some embodiments, the polymer is DNA or RNA. Still, sometimes the nucleic acid is genomic DNA. In other embodiments, the RNA is mRNA, siRNA, or RNAi.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising", or "having", "containing", "involving", and variations thereof as recited herein, is meant to encompass the items listed thereafter and equivalents thereof as well as additional items.

Further features and advantages of the present invention, as well as the structure of various embodiments, are described in detail below with reference to the accompanying drawings.

BRIEF DESCRIPTION OF DRAWINGS

The Figures are illustrative only and are not required for enablement of the invention disclosed herein.

Various embodiments of the invention will now be described by way of example, with references to the accompanying drawings, in which.

DETAILED DESCRIPTION

Figure 1:
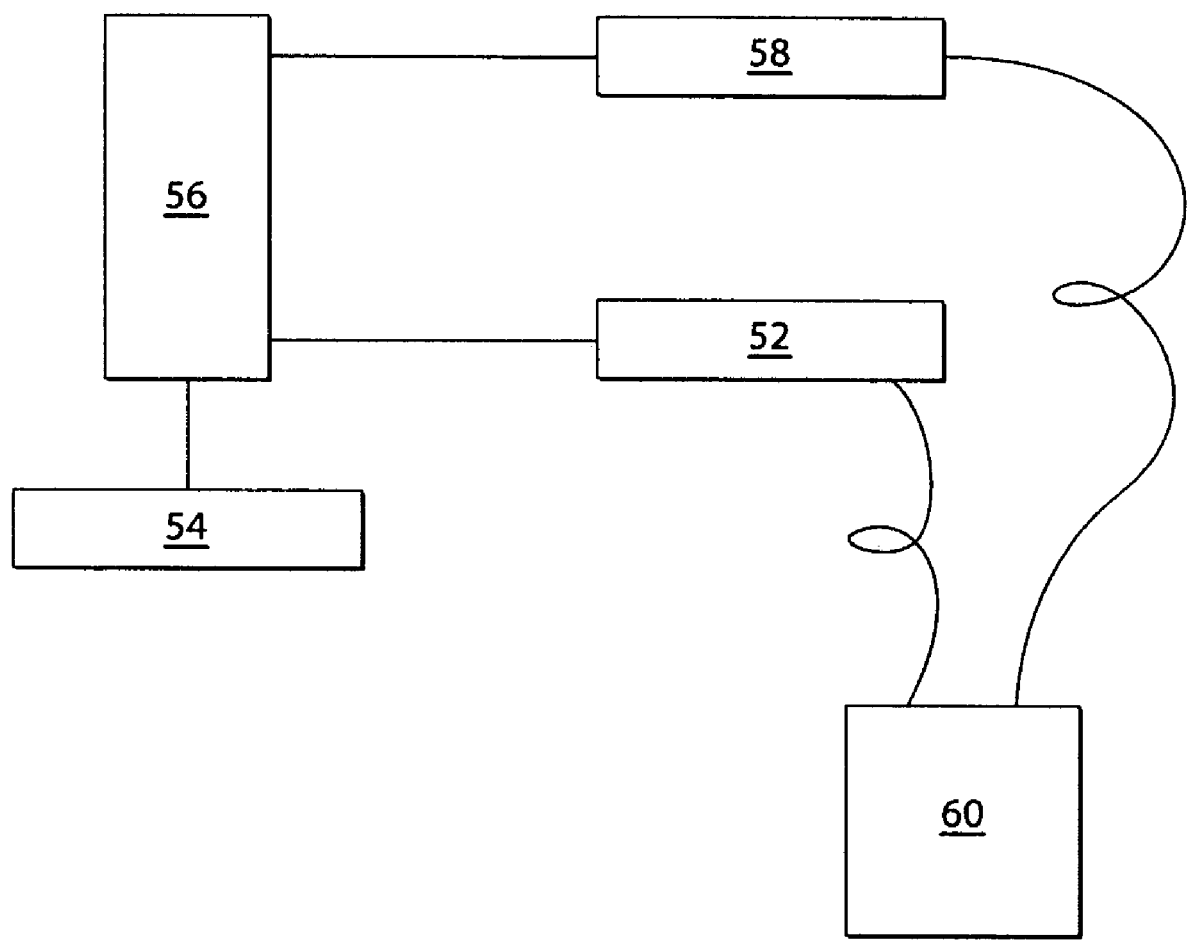
FIG. 1 shows a representation of a detection system and several of the components that comprise many embodiments of detection systems.

The present invention relates, in part, to a detection system for accepting a polymer that has been labeled, an emitter for emitting an excitation signal to excite the label causing it to emit an emission signal, a detector adapted to detect the emission signal as a part of an entire detection signal that is received from a detection zone, and a data processor to analyze the detection and/or emission signals received by the detector. Various aspects of the present invention relate to improving the ability of the detection system to recognize labels within the detection zone, particularly in view of noise or disturbances that might be present in the system.

As used herein, the term "emission signal" is used to denote the emissions of a label, such as the fluorescent or radioactive emissions of some labels. In this regard, an emission signal is defined by the label that provides it. The term "detection signal" is used to denote an entire signal received from the detection zone of a system, regardless of how many emission signals it may contain and/or the amount and type of noise or disturbances that it may also contain. In this manner, the detection zone and its contents define the detection signal.

It is to be understood that when emissions signals are said to be "overlapped", it is meant that each of the emissions signals comprise at least a portion of photons that share a common wavelength in the electromagnetic spectrum.

As used herein, the term "sample area" is used to define a portion of a detection system adapted to accept a sample for analysis. The sample may include a polymer but is not limited to the polymer alone. For example, the sample may include the polymer and a buffer solution along with any other elements floating within the buffer solution.

As used herein, the term "excitation signal" is used to describe the emissions of an emitter that may be used to excite a label. As used herein, the term "excitation zone" defines an area illuminated by an excitation signal of an emitter.

As used herein, the term "detection signal" is used to define all of the optical signal that is received by the optics of a detection system. For instance, this may include reflected excitation signals, noise, emission signals, and the like, that are received by an objective lens or microscope of a detection system.

As used herein, the term "detection zone" is used to denote the zone within a sample area from which optical emissions are received by detectors in the system. This may include all or a portion of an excitation zone and/or all or a portion of a sample area. In many systems, the detection zone may be defined by a confocal aperture that restricts which portions of a detection signal are passed to a detector. In other systems, particularly those using wide field imaging detectors, the detection zone may be defined by all that the wide field imaging detectors are adapted to observe.

As used herein, the term "multi-channel" is used to denote a detection system adapted to detect multiple labels. In particular, it is used to denote a system adapted to detect labels each associated with a particular portion of the electromagnetic spectrum.

As used herein, the term "normalized intensity" particularly when used with reference to an emissions signal, is used to describe an emissions signal that has been divided by its maximum value such that it may be compared with other emissions signals on a normalized basis.

Some aspects of the present invention include one or more particular lasers for exciting one or more particular labels that are used within the system. In such embodiments, the lasers and labels are chosen such that the excitation signals of the lasers do not adversely impact any of the emission signals of the labels to a degree that impedes detection of the labels. Alternatively, the labels may be chosen such that each of their emission signals do not adversely affect the analysis of any other labels within the system. In many embodiments, the labels are fluorophores.

Other aspects are directed to reducing or eliminating portions of detection signals that are associated with extraneous labels residing within the detection zone. In this regard, these aspects focus on reducing or eliminating the possibility of emission signals, such as from additional polymers or unbound labels within the detection zone, being associated with an emission signal from a primary polymer that is being detected or analyzed.

Still other aspects are directed to reducing noise emanating from points out of the focal plane when detecting the labels with wide field imaging devices. In some embodiments, the illumination of the sample area is held substantially within the focal plane of the wide field detector. Thus, only portions of the detection zone lying within the focal plane of the wide field imaging device are excited by the emitter, which reduces or eliminates contributions to the detection signal from outside of the focal plane.

According to another aspect, instrumentation is included within the system to assist wide field imaging devices in differentiating between emission signals at different wavelengths. In this regard, the number of detectors required by some multi-channel systems may be reduced, thus potentially reducing the cost and complexity of the detection system.

Still other aspects are related to using detectors that optimize the benefits of point detection and wide field detection. In such systems, an array of point detectors, such as in a linear CCD array, may be disposed about a sample area to increase the size of the detection zone and the probability that a polymer passing through will be detected while only requiring single linear array for detection.

Turn now to the figures, and particularly FIG. 1, which shows basic components of many embodiments of detection systems. Central to the detection system is a sample area where a labeled sample, such as a polymer or multiple polymers, is directed for detection. An emitter 52, such as a laser, emits an excitation signal that is projected into the sample area 54 such that it may strike a labeled polymer and cause the label to emit an emission signal. If the label is within a detection zone, which may comprise a portion of the sample area or all of the sample area, the emission signal will be a portion of a detection signal that is received by optics 56 of the detection system, such as a lens or microscope. The optics of the system receive the detection signal and directs it through various optical signal processing instruments, such as objective lenses, filtering lenses or mirrors, and the like. Such optical signal processing instruments may be used to extract an emission signal from other portions of the detection signal, including noise, disturbances, etc. After an emission signal, or a portion thereof, has been extracted from the detection signal, the emission signal may be directed to a one or more downstream detectors 58 in the system. The downstream detectors convert the optical signal into an electrical signal for processing by a data processor 60, which is typically a digital computer. The data processor receives the emission signal and analyzes it along with other inputs, such as the spatial location of the polymer relative to the detector, time when the emission signal was detected, the spatial or temporal relationship between the emission signal and other emission signals that are detected, or other characteristics that may be used by a particular detection analysis system.

Multi-Channel Detection Systems

In one illustrative embodiment of the invention, a system and method are adapted to analyze a plurality of labels disposed on a polymer in a manner that prevents an emission signal of one label from acting as a disturbance to another emission signal. In this manner, the labels are less likely to be confused with one another or other components of the detection signal and are thus more likely to be detected. As is to be appreciated, it is generally desirable to distinguish different types of labels of a single polymer so that greater amounts of information may be extracted from the polymer than might otherwise be possible.

Figure 2:
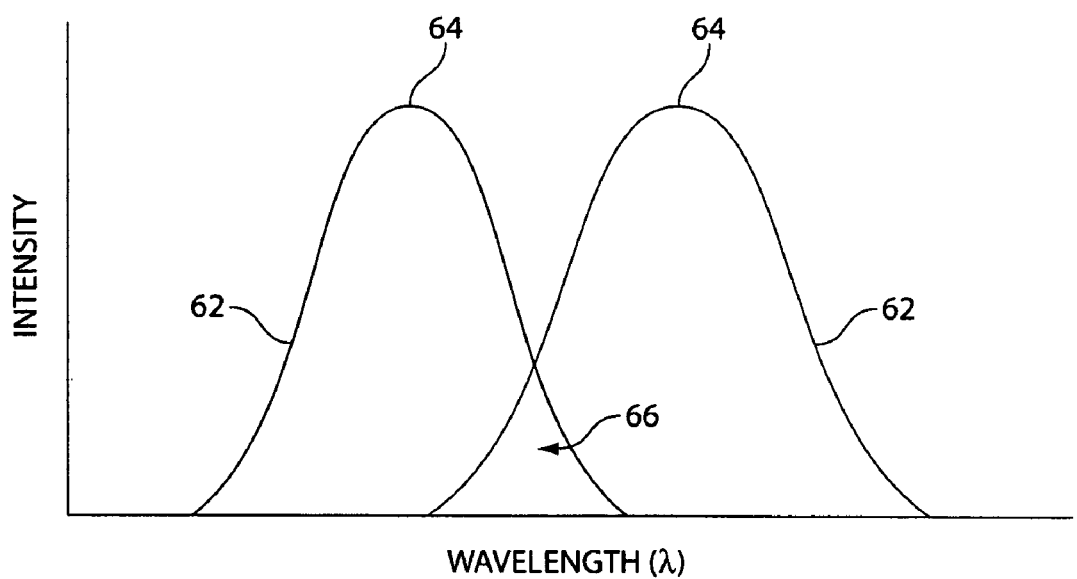
FIG. 2 shows an intensity versus wavelength representation of a detection signal having two emission signals sharing overlapping wavelengths.

In illustrative embodiments of the invention it is desirable to choose labels having distinct emission signals, as is described in U.S. patent application Ser. No. 10/246,779, filed on Sep. 18, 2002, which is hereby incorporated by reference in its entirety. For instance, the labels may be fluorophores having emission signals that lie substantially within a portion of the electromagnetic spectrum associated with a particular color. FIG. 2 shows a plot of two such distinct emission signals included within one common detection signal.

Detectors used in illustrative embodiments of detection systems may be adapted to count photons emitted by labels without regard to the wavelength at which the photons are emitted. In such embodiments, the detectors themselves may be incapable of distinguishing between emission signals from different labels without the assistance of other processing instrumentation. Examples of detectors that may not be adapted to recognize the particular wavelength at which photons are emitted include, but are not limited to, some forms of avalanche photon detectors and Charge Coupled Devices (CCD's).

In some embodiments, filtering devices such as dichroic mirrors may be used to extract and direct emission signals to detectors that might not otherwise be able to distinguish them. In this manner, embodiments of the detection system may be able to detect a plurality of labels that each emit a signal associated with a distinct portion of the electromagnetic spectrum. Such detection systems may be said to be capable of detecting multiple colors, as the emission signals may lie in portions of the visible spectrum that are associated with a particular color. Such multi-color systems may also be referred to as multi-channel systems, as each portion of the wavelength range may be converted into its own electrical signal and analyzed in its own channel of the data processor.

In one embodiment of the invention, dichroic mirrors are used to separate distinct emission signals from a detection signal and direct each of the emission signals to a corresponding detector. Dichroic mirrors operate by allowing certain wavelengths of light to pass through the mirror, while reflecting other wavelengths of light away from the mirror. Most of such dichroic mirrors are characterized by a response curve that defines which wavelengths of light are transmitted and which are reflected, and the gain values associated with the transmission or reflection of each wavelength. An example of a such response curve for a dichroic mirror is shown in FIG. 3.

Figure 3:
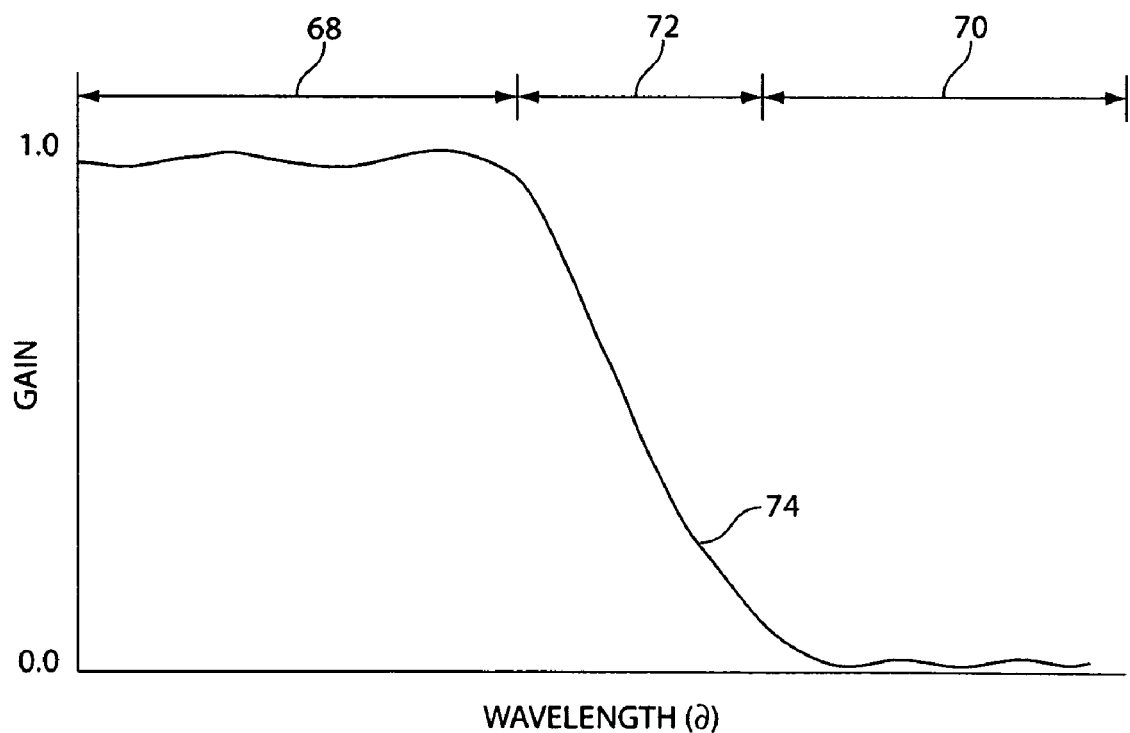
FIG. 3 shows a gain versus wavelength representation of a response curve for a dichroic mirror.
Figure 4:
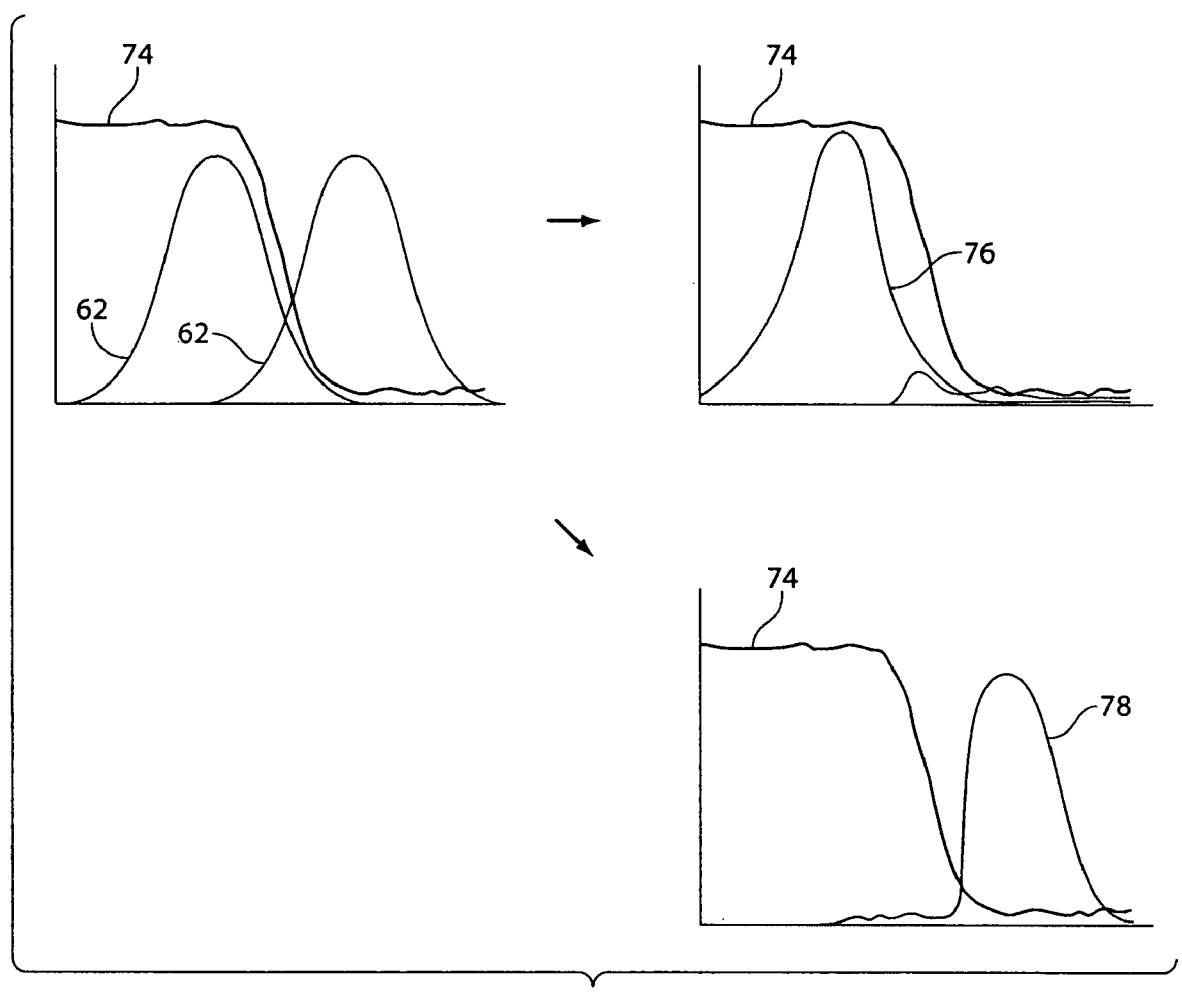
FIG. 4 shows the detection signal shown in FIG. 2 being reflected and transmitted by a dichroic mirror that has a response curve like that shown in FIG. 3.

FIG. 4 depicts a pair of emission signals overlaid with a response curve like that shown in FIG. 3. FIG. 4 also shows the resulting reflected and transmitted signal 76. As used herein, the transmitted signal is the portion of the signal that passes through the mirror while the reflected signal 78 is the portion of the signal that is reflected by the mirror. Here, the transmitted signal comprises a signal having a distribution of intensities substantially equal to the original overlapped signal multiplied by the gain of the response curve at each wavelength. The reflected signal comprises a signal having intensities substantially equal to the original, overlapped signal multiplied by one minus the gain value of the response curve at each wavelength. The transmitted and reflected signals are typically directed in two different directions, such as toward different detectors or different mirrors in the detection system.

In illustrative embodiments of the invention, dichroic mirrors, or other processing instrumentation, may be used to divide signals from one another such that less expensive detectors can be used to detect emission signals in a detection system. However, emission signals 62, although distinct, may still overlap at some wavelengths like the first and second emission signals shown in FIG. 2. As is to be appreciated, dichroic mirrors only split the signal according to a response curve, and are not necessarily capable of separating overlapped portions 66 of the emissions signals strictly according to which label they came from. In this regard, the transmitted signal and/or the reflected signal from a dichroic mirror may contain photons from both of the distinct emission signals at wavelengths where the signals are overlapped.

Practical limitations in many signal processing instruments such as dichroic mirrors, may also limit the ability of a system to separate distinct emission signals. Although ideally the response of a dichroic mirror transitions abruptly between the transmission band 68 and the reflection band 70, most mirrors typically have a transition band that spans anywhere between 30 and 100 nanometers, as shown in FIG. 3. Portions of a signal that reside within the transition band will be both transmitted to a degree and reflected to a degree. This will be defined by the response curve 74, and will depend on the corresponding gain value of the response curve. In this regard, the transition band 72 of a dichroic mirror presents another factor to consider when labels, emitters, and signal processing instruments, such as dichroic mirrors, are chosen for a detection system.

Detection systems may be designed to accommodate overlapped emission signals, transition bands in signal processing instrumentation, and other factors that may prevent an emission signal from reaching a detector in whole form. As represented by the signal intensity versus wavelength graph of FIG. 2, a greater number of photons per wavelength (i.e., intensity) are emitted at and about the emission maximum 64 of a signal. As is to be appreciated, some embodiments of detectors will "detect" a label after a predetermined number of photons have been counted. As is to be further appreciated, the predetermined number may be less than the total number of photons that comprise an emission signal. In fact, this is preferred in many embodiments to compensate for portions of a signal that may be lost during the signal processing steps or due to other imperfection within the system. The portions of a signal at wavelengths further from the emission maximum are less important to signal detection in some embodiments, as they are of a lower intensity and represent a smaller portion of the photons that comprise a given emission signal.

Other factors within the system may also make portions of the signal that are further from the emission maximum less important to detection of an emission signal. For instance, detectors are often limited by their quantum efficiency, which is defined as the ratio of photons that are actually detected to those that are incident upon the detector. The quantum efficiency of some detectors is proportional to the intensity of the incident signal. Those portions of a signal at wavelengths further from the emission maximum, which are of a lower intensity, are less likely to be recognized by a detector if they are incident upon it. In this regard, quantum efficiency is another factor suggesting that portions of an emission signal further from the emission maximum are less critical to detection of an emission signal and consequently, the associated label.

As is to be appreciated, it may be desirable to use many distinct probes and labels on a given polymer to allow more information to be extracted from a polymer when as it passes through a detection zone. However, at least for the aforementioned reasons, it is also to be appreciated that increasing the number of distinct labels and thus the number of distinct emission signals that a detection system is required to distinguish may also cause complications in a system. For example, it may also increase the likelihood that distinct emission signals will overlap at some wavelengths and thus might be confused with one another. To optimize among these factors, embodiments of the invention include methods for choosing labels to reduce the possibility that emission signals will be confused with one another during detection while also providing for more labels in the detection system.

In one illustrative embodiment, the analysis techniques provide for distinguishing multiple emission signals based on the fact that they do not overlap above particular intensities. As represented in FIG. 2, most emission signals may be characterized as having an emission maximum at a particular wavelength and intensities that decrease at wavelengths further from the emission maximum along either direction of the electromagnetic spectrum. As discussed above, some detectors rely on photon counts to detect the presence of an emission signal, and are incapable of determining where photons emanate from within the electromagnetic spectrum. Thus, in some embodiments, detection signals are filtered to remove portions of the signal at wavelengths other than those within a band associated with a particular emission signal. The signals are then directed to a detector such that photon counts may be made. However, where emission signals from different labels overlap over ranges of wavelengths, it may become difficult to extract an emission signal from the detection signal without also affecting the overlapped emission signal.

As previously discussed, a majority of photons for a given emission signal emanate at or near the wavelengths of the emission maximum. Thus, if emission signals overlap at lower intensities, it is less problematic for a detection system. In this regard, embodiments of the present invention may be adapted to have labels with emission signals that do not overlap above intensities of a particular value. This may assist embodiments of the invention in distinguishing emission signals from one another.

Figure 5:
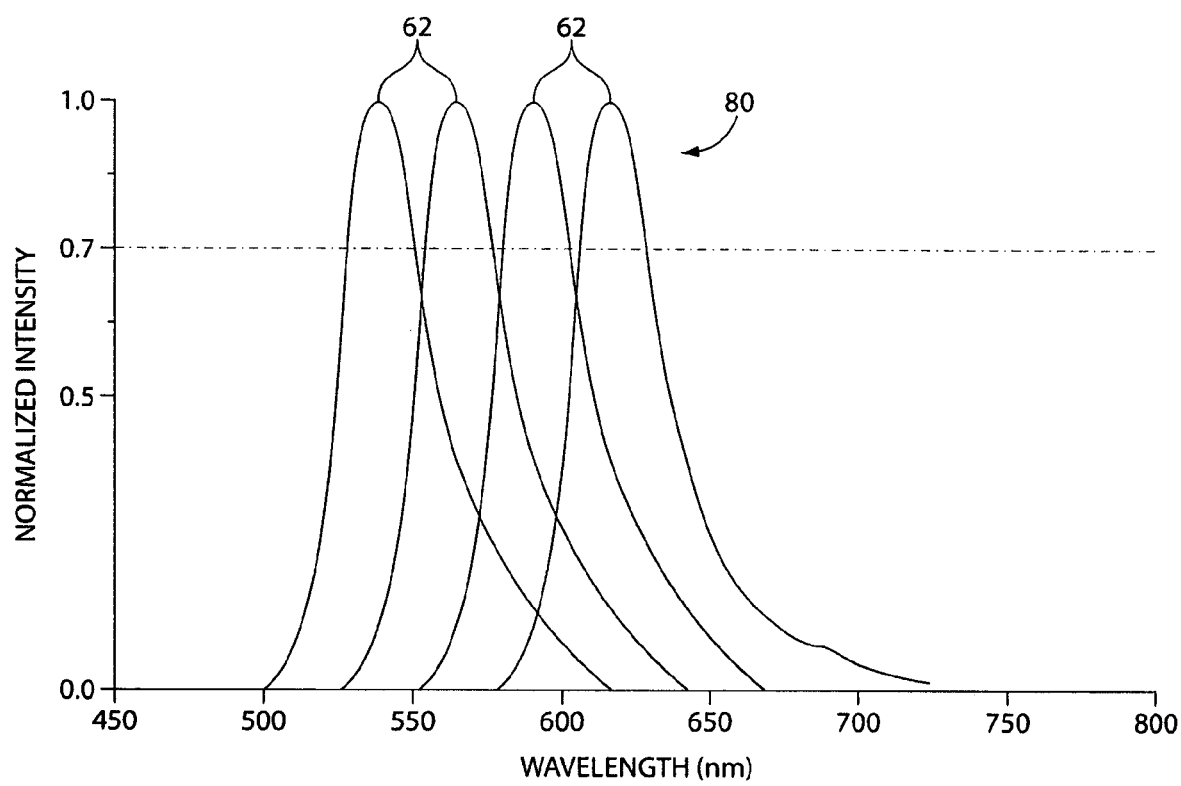
FIG. 5 shows an intensity versus wavelength plot of four emission signals that comprise a particular detection signal.
Figure 6:
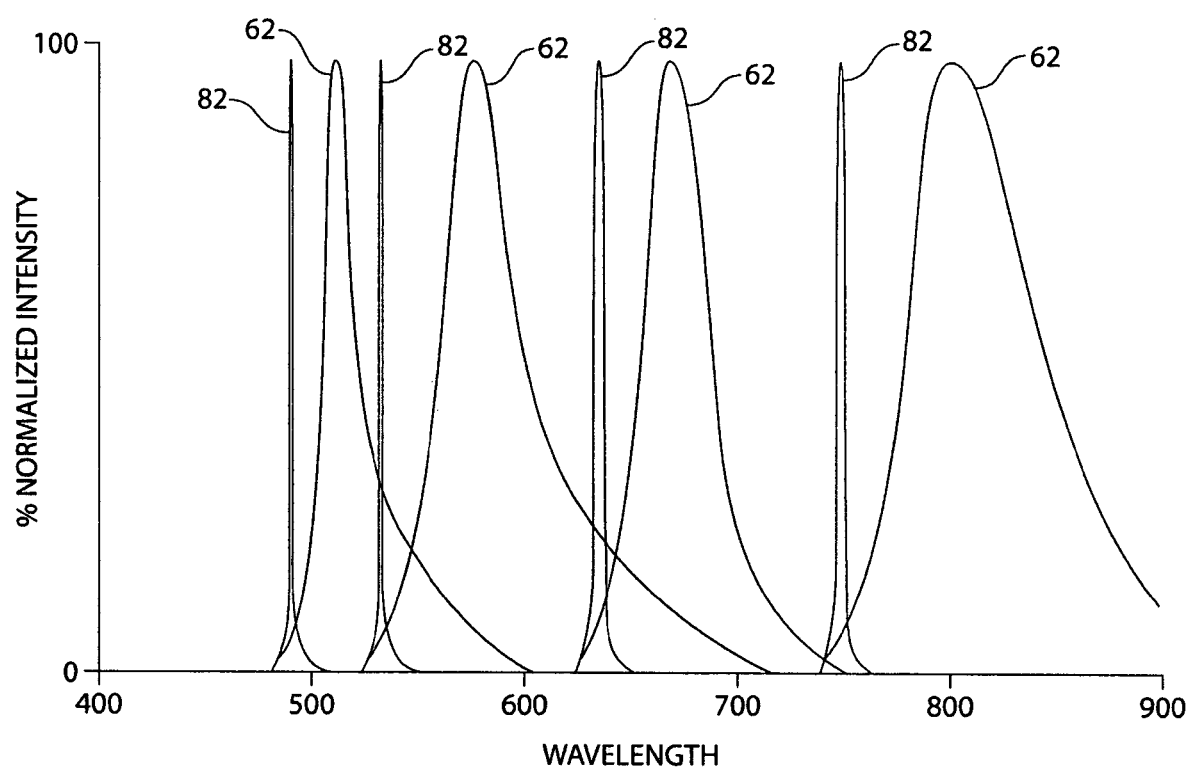
FIG. 6 shows a set of emission signals and the excitation signals used to cause the labels to emit each of the emission signals.

As described above, it may be desirable in some embodiments to use labels characterized by emission signals that do not overlap at points above a certain intensity. In some embodiments using a plurality of labels with emission signals that do not overlap above 70% of the maximum, normalized emission signal intensity, as shown in FIG. 5. Here, intensity is measured in terms of total photon count per unit wavelength and the emission signals are normalized to one another by dividing each emission signal intensity curve by its maximum intensity value, as is reflected by the emission signal curves shown in FIG. 5, and provides emission signals that can be separated such that they can be detected by the system with a high degree of confidence. In other embodiments, labels may be chosen such that there is no overlap above 50% of the maximum, normalized intensity to accomplish this effect. Still, in other embodiments labels may be chosen such that there is no emission signal overlap at points above 30% of the maximum, normalized emission signal intensity to allow distinct emission signals to be detected with confidence. FIG. 6 shows a graph of four emission signals that do not overlap above 30% of the maximum, normalized signal intensity. In other embodiments, the emission maximums of the signals, the labels they represent (fluorophores in this embodiment), their associated excitation frequencies, and lasers that may be used to excite the labels may be those listed in Table 1 below.

TABLE 1

| Channel | Laser | Wavelength (nm) | Label | Excitation Max. | Emission Max. |
|---|---|---|---|---|---|
| Blue | Sapphire | 488 | BODIPY FL | 504 | 512 |
| Green | YAG $2^{nd}$ harmonic | 532 | Tamra | 553 | 575 |
| Red | HE-Ne | 633 | Alexa 647 | 650 | 665 |
| IR | Alexandrite | 750 | Alexa 750 | 749 | 775 |
|  |  |  | IR 38 | 778 | 806 |

In one illustrative embodiment of the invention, labels are chosen such that their emission maximum are separated from one another by no less than a predetermined number of wavelengths to prevent portions of any emission signal, such as overlapping portions, from interfering with another emission signal. For example, in one embodiment, the labels are chosen such that their emission maximums are separated by more than substantially 60 nanometers. The labels reflected in Table 1 above also meet this criteria.

In some illustrative embodiments, the excitation signal used to excite the label, typically the coherent light of a laser, may also be reflected toward the detectors of the system as part of the detection signal 80. The excitation signal 82, if not removed from the detection signal, may be incorrectly considered part of an emission signal. As is to be appreciated, it is desirable to extract any portions of the excitation signal from the detection signal and thus any emission signals therein, without impacting the emission signals so much that the emission signal might be misinterpreted by, or not detected by the detection system.

As described above, it is desirable to remove as much of the excitation signal from the detection signal without impacting any emission signals too much. Having portions of an excitation signal present in an emission signal may cause incorrect photon counts as excitation signals typically include high intensity light may provide a high number of photons to a detector. The high number of photons associated with the excitation signal may have a greater impact on the photon count of a detector than other noise within a system. To help reduce any impact on the emission signals, lasers or other excitation signals may be chosen such that they are located at wavelengths that are substantially separated from the emission maximums of any labels used within the detection system. In this manner, removing the excitation signals from the emission signals may be accomplished without adversely affecting the emission signal at points near an emission maximum.

In one illustrative embodiment, combinations of lasers and fluorophores are chosen such that each excitation signal is separated by about 20 nanometers or more from the emission maximum of all fluorophores used in a detection system. For example, FIG. 6 shows excitation signals overlaid on a graph of the emission signals for four distinct labels. The excitation signals and the emission signals represented in FIG. 6 are those of Table 1. It is to be noted that Table 1 includes both an Alexa 750 and an IR 38 label that can be used interchangeably to accomplish similar effects.

Choosing excitation signals as described above may require the excitation signal to deviate from the optimal excitation wavelength for a particular label. For example, this may mean having an excitation signal wavelength set at 488 nm to excite a fluorophore with an optimal excitation wavelength of 504 nm. However, in many embodiments, the tradeoff is worthwhile, as otherwise the excitation signal might not be removed from a detection signal in the system without also removing portions of the emission signal that are closer to the emission maximum. Table 1 also reflects the excitation maximums of various labels represented in FIG. 6.

In one illustrative embodiment of the invention, the detection system includes an optical instrument for extracting each of the excitation signals from the detection signal. A polychroic mirror 84 is an example of an instrument that may be used to accomplish this. The polychroic mirror, like a dichroic mirror 86, is adapted to transmit particular wavelengths of light and reflect other wavelengths of light. However, the polychroic mirror comprises multiple transmission bands and multiple reflection bands, whereas a dichroic mirror typically has a single transmission band and a single reflection band. In this regard, a single polychroic mirror may be used to remove, or reflect in a different direction, several distinct bands of a detection signal, such as the excitation signals.

As with the dichroic mirrors discussed above, the polychroic mirror is characterized by a transition band disposed between each of the transmission and reflection bands. Preferably, the transition band spans a narrow range of wavelengths such that only narrow bands of a detection signal associated with the excitation signals are removed when passing through the polychroic mirror. Having a shorter transition band in the polychroic mirror is generally more important when the signal to be separated, in this case the excitation signal, is closer to the emission maximum of the emission signal. In this regard, techniques for improving the cutoff rate between the reflection and transmission bands of the mirror are typically used. One such technique includes using rugate technology to manufacture the mirror.

Figure 7:
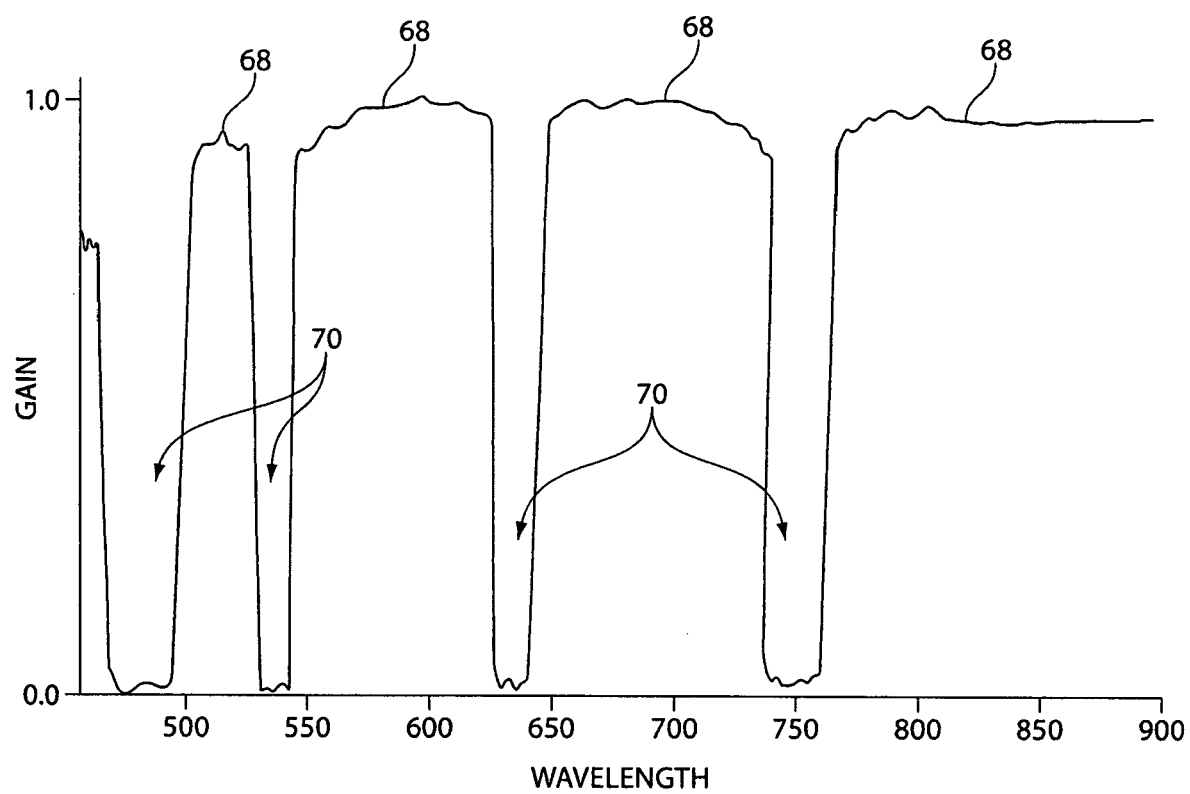
FIG. 7 shows a response curve for a polychroic mirror used to remove excitation signals from a detection signal, according to one embodiment of the invention.
Figure 8:
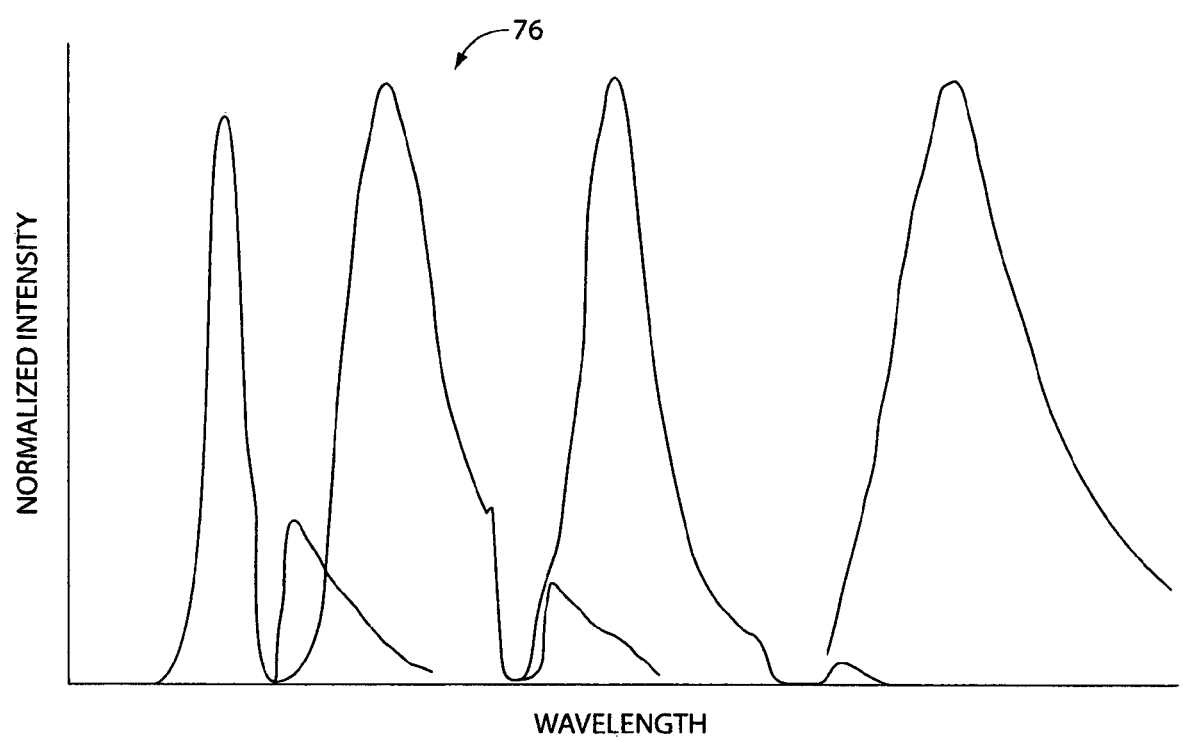
FIG. 8 shows the detection signal of FIG. 6 after having been passed through a polychroic mirror like that represented by FIG. 7.

Polychroic mirrors employing rugate technology, and sold as discrete rugate match filters, can be purchased from Barr Associates of Westford, Mass. Such polychroic mirrors may be made having transition bands sharp enough to remove excitation signals associated with the lasers of Table 1, or other excitation signals, without affecting the emission signals also shown in Table 1 to a such a degree that they are incorrectly detected by the system. FIG. 7 shows a representative response curve for such a polychroic mirror. Also, FIG. 8 shows the emission and excitation signals of FIG. 6 after being passed through a polychroic mirror having a response curve like that shown in FIG. 7. As can be appreciated, the polychroic mirror not only reflects the excitation signals, but also any portion of the detections signal within the reflection bands of the polychroic mirror, such as portions of an emission signal.

In one illustrative embodiment of the invention, once the excitation signals are removed from the detection signal, the various wavelength bands associated with the emission signals in the system are separated for independent detection by detectors of the system. A detection signal containing emission signals of multiple labels may be passed through one or more dichroic mirrors to separate the various emission signals out of the detection signal and direct them to an appropriate detector. Some representative schemes for separating the emission signals from a detection signal are discussed below.

Figure 9:
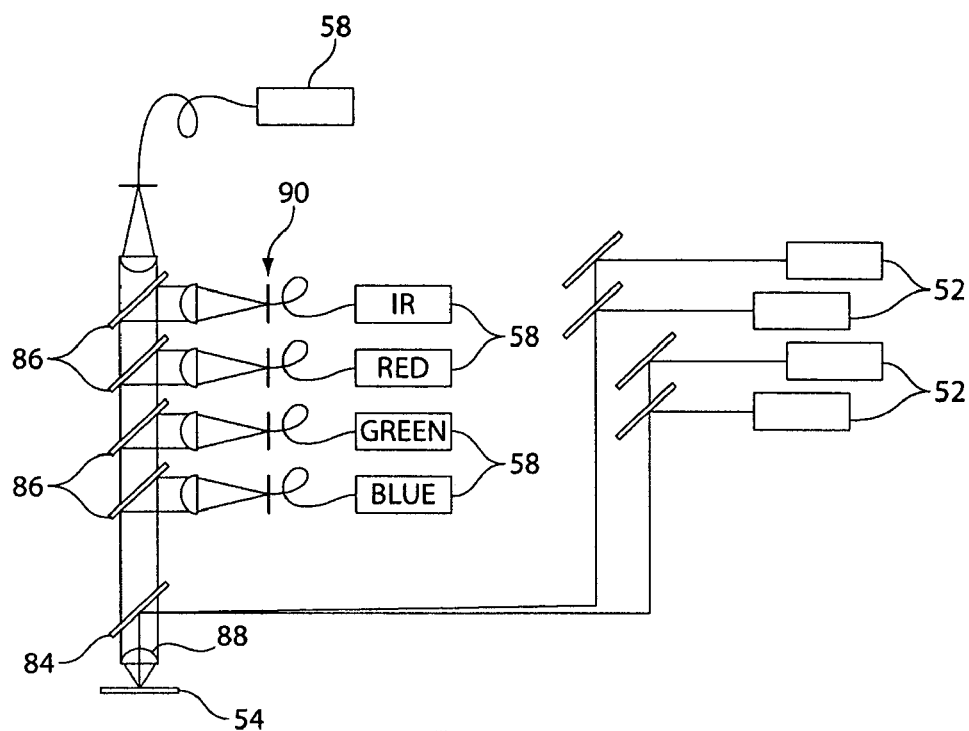
FIG. 9 is a schematic diagram of a detection system, showing dichroic mirrors extracting emission signals from a detection signal according to an embodiment of the present invention.

An example of a system used to separate the emission signals from a detection signal is shown in FIG. 9. Here, a detection signal is passed through a series of dichroic mirrors that each reflect a portion of an emission signal from the detection signal and direct it toward a detector. The first dichroic mirror receives the entire detection signal and reflects portions below the cutoff wavelength of the first dichroic. The cutoff of the first dichroic is set above the emission maximum wavelength of the emission signal having the shortest wavelength, yet below the emission maximum of the emission signal having the next largest set of wavelengths in the system. In this manner, the first dichroic reflects any emission signal associated with the shortest wavelength (e.g., blue) of the detection signal and toward a detector for the corresponding (e.g., blue) channel of the system. The remaining portions of the detection signal are transmitted to the next dichroic mirror, which then reflects portions of the detection signal below its cutoff wavelength, which is above the next channel in the system characterized by the next longest wavelength (e.g., the green channel). The green emission signal is, in turn, directed toward a detector that may be optimized to detect signals within the green portion of the electromagnetic spectrum. This process continues with each subsequent mirror having a cutoff wavelength set to remove the emission signal characterized by the next longest wavelength. In this manner, each of emission signals may be removed from the detection signal and provided to detectors that might not otherwise be able to distinguish between emission signals, and thus between labels. However, it is to be appreciated that other methods of separating the detection signal into separate emission signals, or extracting various emission signals from the detection signal may also be used, as the present invention is not limited to the above described method.

Figure 10:
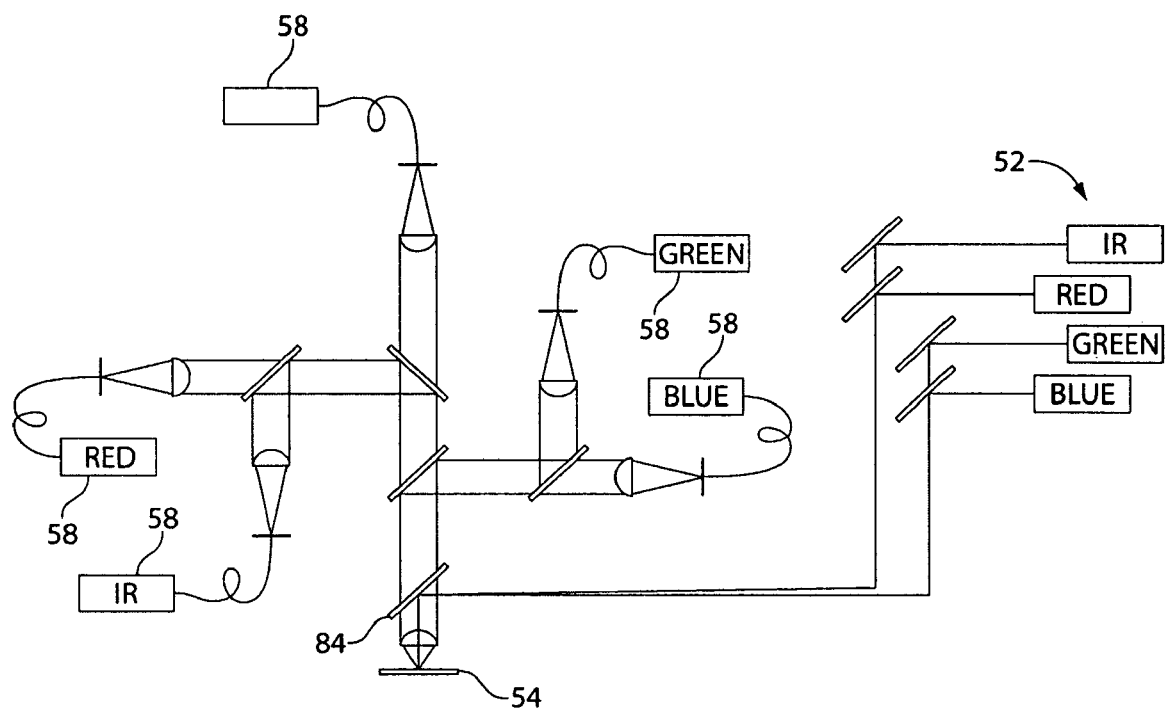
FIG. 10 is a schematic diagram of a detection system, showing dichroic mirrors extracting emission signals from a detection signal according to another embodiment of the present invention.

In another illustrative embodiment, as represented in FIG. 10, after having removed excitation signals with a polychroic mirror or equivalent approach, the detection signal is directed to a first dichroic mirror having a response curve adapted to reflect the two emission signals having the two shortest wavelengths. In the illustrated embodiment, this includes the blue and green emission signals. The remaining red and infrared signals are transmitted through the first dichroic mirror. Thereafter, the portion of the detection signal comprising the blue and green emission signals is passed through an additional dichroic mirror, which transmits the blue signal and reflects the green signal. After passing through this second dichroic mirror, each of the blue and green signals are directed to a detector adapted to detect each of the blue and green signals, respectively. Like the portion of the detection signal comprising the blue and green signals, a portion containing the red and infrared signals is directed through an additional dichroic mirror that transmits the red emission signal while reflecting the infrared signal. Each of the red and infrared signals are then directed to detectors adapted to detect the red and infrared emission signals, respectively. Although the above embodiment is described as having four different emission signals, each corresponding to a portion of the electromagnetic spectrum, other numbers of distinct labels and thus emission signals may be used by the detection system, as the present invention is not limited to four distinct labels.

In one illustrative embodiment, the detection signal or separated emission signals may be passed through an additional bandpass filter, other than the polychroic mirror designed specifically to remove excitation signals. In this manner, the bandpass filter may serve to further reduce noise from the detection or emission signal, thereby improving the quality of the analysis performed by the detection system. Such a multiple bandpass filter may be placed anywhere within the flow stream of the detection signal. For instance, it may be placed immediately downstream or upstream from one or more of the polychroic mirrors, or it may be placed downstream from any one of the dichroic mirrors. It is to be understood that it may even be omitted from the detection system altogether as the invention is not limited to including such a multiple bandpass filter. In one particular embodiment, a bandpass filter with a high degree of rejection (10,000 to 100,000 fold) is placed upstream of every detector such that unwanted scattered light is suppressed or removed from the optical signals before they are passed to the detectors.

Various types of detectors known to those of skill may be used in detection systems of the present invention. In one illustrative embodiment, each of the emission signals, after being extracted from the detection signal, is directed to avalanche photon detectors where photons are counted. The photon counts, or lack thereof, may be used to determine whether a particular label is present on a polymer at a given time. These counts may be collected and measured relative to the time at which they are collected. Alternatively, they may be collected for a given still image within the detection zone at a known time. In other embodiments, emission signals separated from a detection signal may be directed to a CCD detector, where their intensity may be detected about an array, either a linear array or a two dimensional array, of the CCD device. The present invention is not limited to any specific type of detector.

Having described several components that may be used in embodiments of the detection system, such as dichroic mirrors, polychroic mirrors, bandpass filters, detectors, emitters, and the like, it is to be appreciated that they may be incorporated into a detection system in various different schemes. However, aspects of the present invention are not limited to the embodiments disclosed and discussed above, as those of skill will recognize that instrumentation may be substituted and signal processing schemes may be altered without departing from various aspects of the invention. For example, although many of the illustrative embodiments have described a system having four channels, (i.e., four distinct labels, each associated with particular wavelengths in the electromagnetic spectrum and its own channel in the detection system), other systems having any number of channels are also contemplated by the invention. For instance, a system having two channels, three channels, or five or more channels are also embraced by the present invention.

Overlapping Detection Zones

As described generally above, embodiments of the detection system may be used to identify when a label bound to a polymer passes through a detection zone and/or the nature of the label. The time when the label passes through the detection zone, measured with respect to other features of the polymer, may be used to discern if, and where, a particular sequence is located on the polymer. To this end, analysis of a polymer by the detection system may involve passing polymers, with labels thereon, through the detection zone within the sample area such that label(s) may be detected.

In many embodiments of detection systems, multiple polymers may be passed through a sample area simultaneously. This may be done for a variety of reasons. For example, in some systems, multiple polymers may be directed through the sample area and the detection zone so that multiple assays may be performed in a single test set up. In other embodiments, multiple polymers may be directed through the sample area and towards a detection zone to increase the probability of a particular polymer passing through the zone. Still, multiple polymers may be directed toward the detection zone for other reasons, as the invention is not limited as to why multiple polymers may exist within the detection zone at a given time.

As can be appreciated for at least the above described reasons, it is advantageous in various embodiments of the invention to direct multiple polymers to a detection zone. However, as can also be appreciated, situations may arise where having multiple polymers within the detection zone at the same time may complicate the analysis of one or all of the polymers. For example, a detection signal may end up containing emission signals from labels of different polymers. Aspects of the present invention may be used to identify which label and polymer the emission signals are from, and in some cases, to eliminate unwanted emission signals.

Other aspects of the invention are useful for distinguishing between emission signals that emanate from different spatial regions of a detection zone. For example, multiple labels of the same or different polymers may reside within different portions of a detection zone at a common time. It may be desirable to isolate each component of the emission signal corresponding to each of the labels to discern their location within a detection zone. Alternately, it may be desirable to eliminate one of the emission signals from a detection signal (e.g., if the emission signal is making it more difficult to discern the presence or type of another label).

In one illustrative embodiment, multiple detection zones may be used to distinguish the spatial origin of a portion of a detection signal. For example, detection zones may be overlapped where a first detection zone is located partially or entirely within a second detection zone. Each detection zone is associated with its own detection signal for downstream data processing. The detection signals from each of the detection zones may be compared with one another to discern which portions of the detection signals are common to both detection zones and which are unique. Those portions unique to either detection signals may derive from non-overlapping portions of the corresponding detection zone. Similarly, those portions common to both detection signals may derive from common portions of the detection zones. In this manner, such an approach may identify the spatial origin of portions of a detection signal.

As previously defined, an excitation zone includes the light emitted by an emitter, such as a laser, or combination of lasers. In many embodiments, the excitation zone may be circular, as is typical of laser beams. In other embodiments, the excitation zone may comprise a substantially rectangular line disposed across the sample area. It may also comprise multiple lasers beams each within the excitation wavelengths of a label that is used within the detection system. By way of example, the lasers may be those listed in Table 1 above. However, it is to be appreciated that the excitation zone is not limited to these lasers, or even to lasers, as it may include any signals adapted to excite a label passing within the excitation zone.

As previously discussed, labels passing through the excitation zone may emit an emission signal that contributes to a detection signal received by the system, particularly when the excited label is within the detection zone. An objective lens 88 may be positioned to receive the detection signal emanating from the detection zone and to magnify the detection signal for subsequent processing. The objective lens may be part of the microscope of the system. Additionally, other contents of the excitation zone may emit signals and some portions of the excitation signals may be reflected into the detection zone, toward the objective lens as a part of the detection signal. In one illustrative embodiment, the objective lens receives the detection signal, including reflected excitation signals and other noise. The objective lens then magnifies the signal between 60× and 100× for processing through a polychroic mirror and multiple dichroic mirrors of the microscope to extract any emission signals within the detection signal, as previously discussed. After extracting emission signals from the detection signal, or performing other optical signal processing steps, the emission or detection signals are then passed through a confocal lens of the microscope that may reduce the optical signal back towards its original magnification, although other reductions are possible, or no reductions may be made, as the present invention is not limited in this regard.

In many embodiments, a confocal aperture 90 is used to remove out of focus portions of the detection signal before the signal is transmitted to a detector. The confocal aperture may be placed at the focal point of the confocal lens and is often sized to block any light not within the focal point. In some embodiments, the confocal aperture may be sized smaller than the entire focal point, such that it not only prevents out of focus light from passing, but also prevents some in focus light from being transmitted. In this regard, portions of the detection signal associated with peripheral portions of the excitation zone, or other portions of the excitation zone, may be prevented from passing there through. In this manner, the confocal aperture may also be used to define the size of detection zone within the sample area. As is to be appreciated, the detection zone need not be the same size or shape as the excitation zone, as the confocal aperture may be sized and shaped to allow only select portions of signals to be transmitted beyond the aperture of the microscope.

After emission signals have passed through the confocal aperture, they are directed to an optical detector for conversion into an electrical signal for downstream data processing. Although many types of detectors may be used, some illustrative embodiments include point detectors, such as avalanche photodiodes or photomultiplier tubes, which convert the photons of the optical signal into an electrical signal for data processing and analysis. The invention is not limited to these point detectors, as other point detectors, or even wide field image detectors may be used as well.

In many embodiments, after passing though the confocal aperture, the emission signals are directed through a fiber optic cable to the detector for conversion into electric signals. For example, after passing through the confocal aperture, the optical signal may be directed onto a receiving end of a fiber optic cable that carries the signal to the detector. The receiving end of the fiber optic cable is typically sized and shaped consistent with the confocal aperture and in some embodiments is fixed within the confocal aperture, although it is not required to be in all embodiments of the invention. Alternatively, in some other embodiments, the receiving end of the fiber optic cable may comprise the confocal aperture, as it may only transmit light that is incident upon its receiving end, which may be a defined cross section sized and positioned to reside within the focal point of the confocal lens. In one illustrative embodiment, the confocal aperture and the fiber optic cable have a circular cross section with a 100 micron diameter that is associated with a 1 micron detection zone (due to 100× magnification). In another embodiment, the confocal aperture and fiber optic cable have a circular cross section with a 50 micron diameter that is associated with a 0.5 micron detection zone. However, the confocal aperture may have any shape or size of cross section, as the present invention is not limited in this respect.

In one illustrative embodiment, the detection system also focuses the detection signal onto the receiving end of an additional, smaller, confocal aperture and associated fiber optic cable. In this regard, the smaller aperture focuses the same detection signal onto a confocal aperture of a smaller size, and thus defines a smaller detection zone that is completely overlapped with a detection zone defined by a larger, confocal aperture that receives the same detection signal. As with the detection signal of the larger detection zone, the smaller detection signal is transmitted to a detector through an optical fiber for subsequent analysis and comparison with the signals transmitted by other detectors within the system, as is discussed in greater detail below. As is to be appreciated, although the above is described with respect to a detection signal, the same may be accomplished with an emission signal after it has been extracted from the detection signal, or any other signals within a detection system, as the invention is not limited in this respect.

In one illustrative embodiment, as described above, one detection signal is separated into bands of the electromagnetic spectrum that are each associated with the emission signals of labels used in the system. Each of the bands may be passed through a confocal aperture, such as a 100 micron confocal aperture, and may then be transmitted to single point detector for converting the optical signal into an electrical signal. Additionally, the detection signal may also be delivered to a smaller circular, confocal aperture having, for example, a 50 micron aperture centered within the focal point of the focused detection signal. In this manner, the 50 micron confocal aperture defines a 0.50 micron detection zone centered within a 1.00 micron detection zone used to provide emission signals to each channel of the detection system. However, it is to be appreciated that the detection zone, and sub-portions of the detection zone may be of any size and/or shape as the invention is not limited to circular detection zones or detection portions. Similarly, the detection zone need not overlap at a central portion of either detection zone, as the present invention is not limited to circular, concentric detection zones.

In one illustrative embodiment, each channel of the detection system may receive an emission signal corresponding to a 1.00 micron detection zone. Also, one separate detector may receive a detection signal corresponding to a 0.50 micron detection zone centered within the larger 1.00 micron detection zone. In this manner, the data processor will receive a signal associated with the smaller detection zone that can be compared with any of the emission signals coming from the larger detection zone. If any of the emission signals are suspected of containing unwanted components that emanate from portions of the larger detection zone not also common with the smaller detection zone, they can be compared with the detection signal associated only with the smaller zone. If the suspect portions of the emission signals are common to both of the detection zones, it may be inferred that they emanate from within the smaller detection zone. However, if the suspect portions of an emission signal are not also present in the detection signal coming from the smaller detection zone, then it may be inferred that the suspect portions emanate from points of the larger detection zone that are not common with the smaller detection zone. The data processor may then decide whether to reject these suspect portions of the emission signal.

As discussed briefly above, labels may emit an emission signal having characteristics that are dependent on the location of the label within the detection zone. For example, some detection zones may be illuminated by a Gaussian laser beam having intensities that vary spatially across a detection zone. A label located in an area of the detection zone having a higher intensity may emit a more intense emission signal. In other embodiments, such as in detection systems where labels are moving relative to the detection zone during analysis, the emission signal emitted by a label may be dependent upon the path the label travels through the detection zone. Such characteristics of an emission signal, taken with respect to the detection zone, may be used by the present invention to improve analysis of the label and thus any polymer it is bound to.

Figure 11:
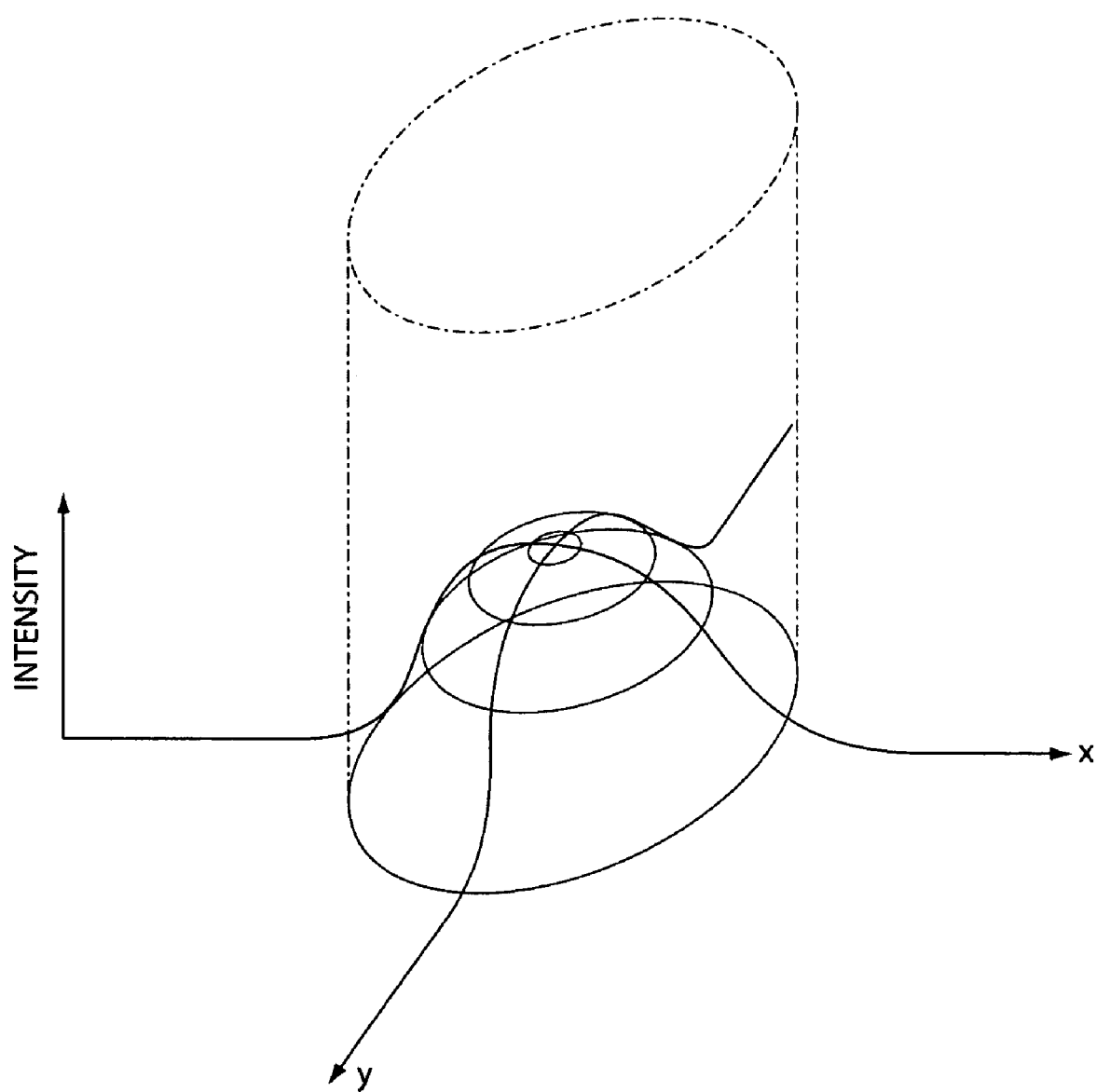
FIG. 11 shows a representation of signal intensity as it varies across the cross section of a Guassian laser beam.

FIG. 11 shows a three dimensional view of laser intensity as it varies with position across a laser beam in one illustrative embodiment. Here, the intensity of the laser follows a substantially Gaussian, two dimensional distribution about its circular cross section. It is to be appreciated that other intensity distributions may also exist, as the Guassian distribution shown in FIG. 11 is merely exemplary of how intensities may vary with position in the cross section of a laser beam, or other excitation signals.

Figure 12:
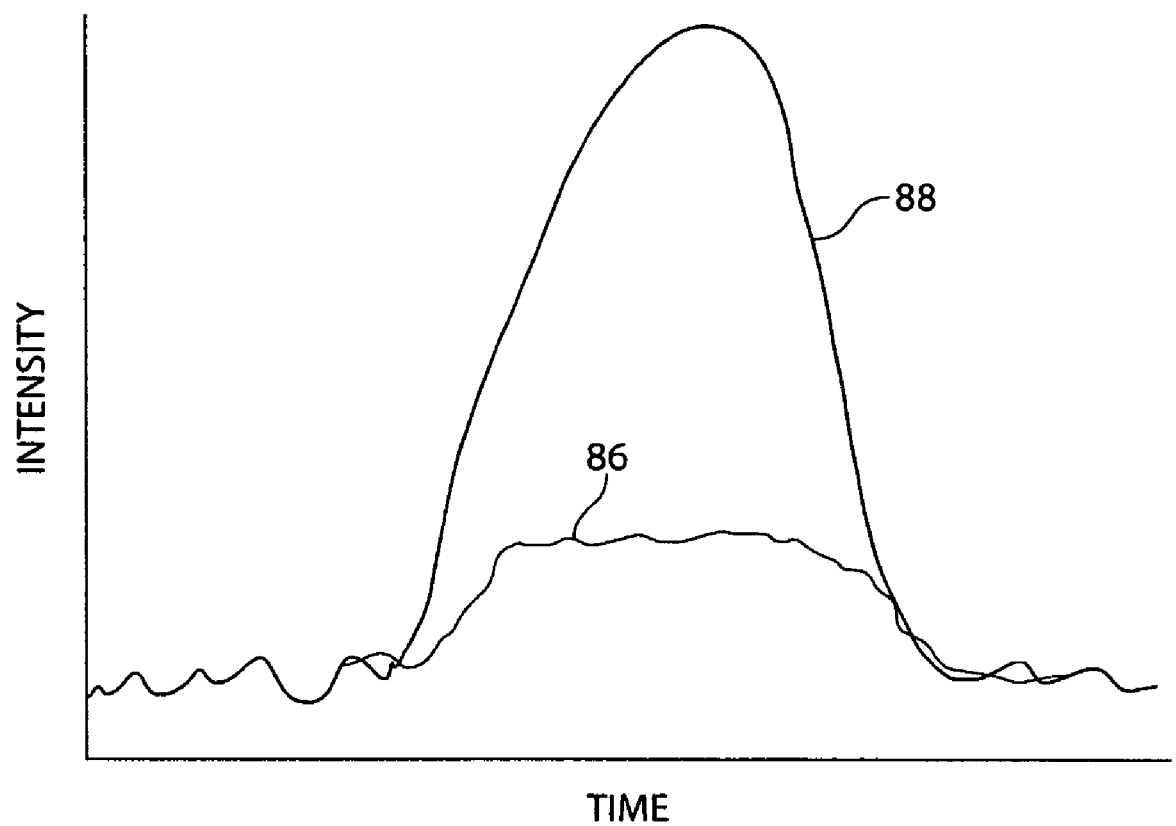
FIG. 12 shows an intensity versus time plot representing a label passing through a high intensity portion of a detection zone and a low intensity portion of a detection zone.

The intensity of an emission signal emitted by a label may vary with the intensity of the excitation signal that it is exposed to. In this regard, a label that is disposed within the low intensity, peripheral portion of an excitation signal, like that represented by FIG. 11 may emit an emission signal of a lower intensity. This is represented in FIG. 12, which shows separate emission signals 86, 88, superimposed on the same graph, of labels located in both a high intensity region and a low intensity region of an excitation signal.

Illustrative embodiments of the detection system are often characterized by a system noise level. Many factors may contribute to the noise level of the system, such as imperfections in the optical instrumentation, impurities in the polymers and/or labels, imperfections in the electronics, disturbances from the ambient atmosphere, and the like. Most systems will be less capable of distinguishing signals, such as emission signals, that are closer to the system noise level, and thus have a lower signal to noise ratio. The emission signal of a label located in the low intensity region of the laser 86, as shown in FIG. 12, is much closer to the noise level, and thus more difficult for the system to recognize. Additionally, the emission signal, if not properly recognized, may actually be contributing to the noise level of the system in some embodiments, thus making it more difficult to detect other labels residing in the detection zone.

In one illustrative embodiment, the emission signals detected by the system include information that is dependent on the path traveled by the label. In many detection systems, the polymers are moved relative to the detection zone while being detected. Some systems may not be able to control the precise placement of the polymer within a detection zone. As such, polymers may pass through a central portion of the detection zone along a path that spans a distance substantially equal to the diameter of the detection zone (for a circular detection zone) and thus pass through a significant portion of the high intensity region. However, some of the polymers may only pass through the detection zone along a chordal line, entering the high intensity region only briefly, if at all. Such path dependence may add to the variability within some systems, thereby adding to the relevance of aspects of the invention used to distinguish between labels passing along only a peripheral edge of a detection zone.

The emission signal emitted by a label may also be dependent on the amount of time the label is resident within the detection zone. As such, the length of the path of travel that a label follows through a detection zone affects the emission signal in addition to the intensity of the detection zone that it passes through. For example, a label following a diametral path line through a circular detection zone will reside in the detection zone longer than a label following a chordal path through the detection zone, all else being constant. The label residing within the detection zone longer will generally emit more photons than a label residing in the detection zone for a shorter period of time. This presents yet another factor that can cause variability, and thus uncertainty, in analyzing which emission signals are within a detection signal.

Figure 13:
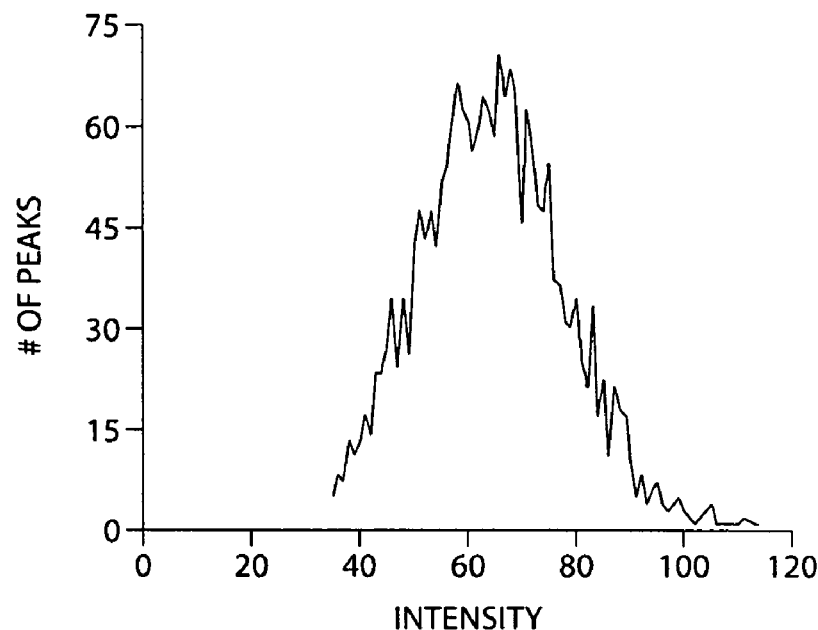
FIG. 13 shows a histogram of a peak intensity associated with a label passing through a central portion of a detection zone, according to one embodiment of the invention.

In one illustrative embodiment, emission signals are analyzed within the detection signal at the data processing stage by evaluating the number of peaks within the detection signal at each intensity level. FIG. 13 shows a graph representative of such an analysis. Here, the peaks are binned according to their intensity level and are then plotted as a histogram. Fitting data from a detection signal in this manner may help distinguish the emission signals from noise within the system. However, as can also be appreciated, labels residing within the low intensity regions of the excitation signal may increase the number of low intensity peaks and confuse the analysis. For example, the low intensity peaks may distort the expected distribution of an emission signal from the expected form shown on FIG. 13 to one like that represented in FIG. 14, which includes additional low intensity peaks. This can cause, in some instances, a misidentification of an emission signal. For example, contributions from a label within the low intensity portion of a detection zone may appear to be part of an emission signal that resides on a polymer within the high intensity region of the detection zone. As is to be appreciated, this may cause the structure of the polymer within the high intensity region to be interpreted incorrectly.

Figure 15:
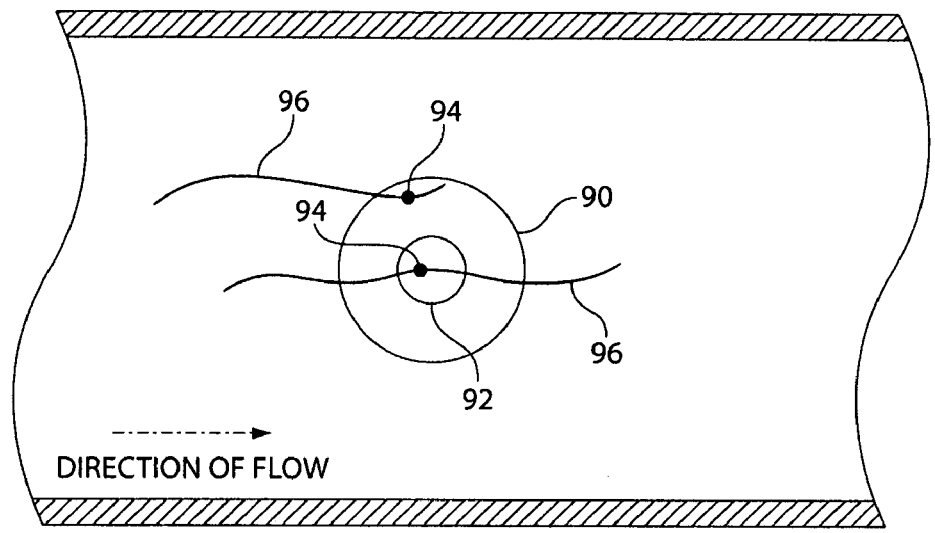
FIG. 15 shows overlapped concentric detection zones, according to an embodiment of the present invention.
Figure 16:
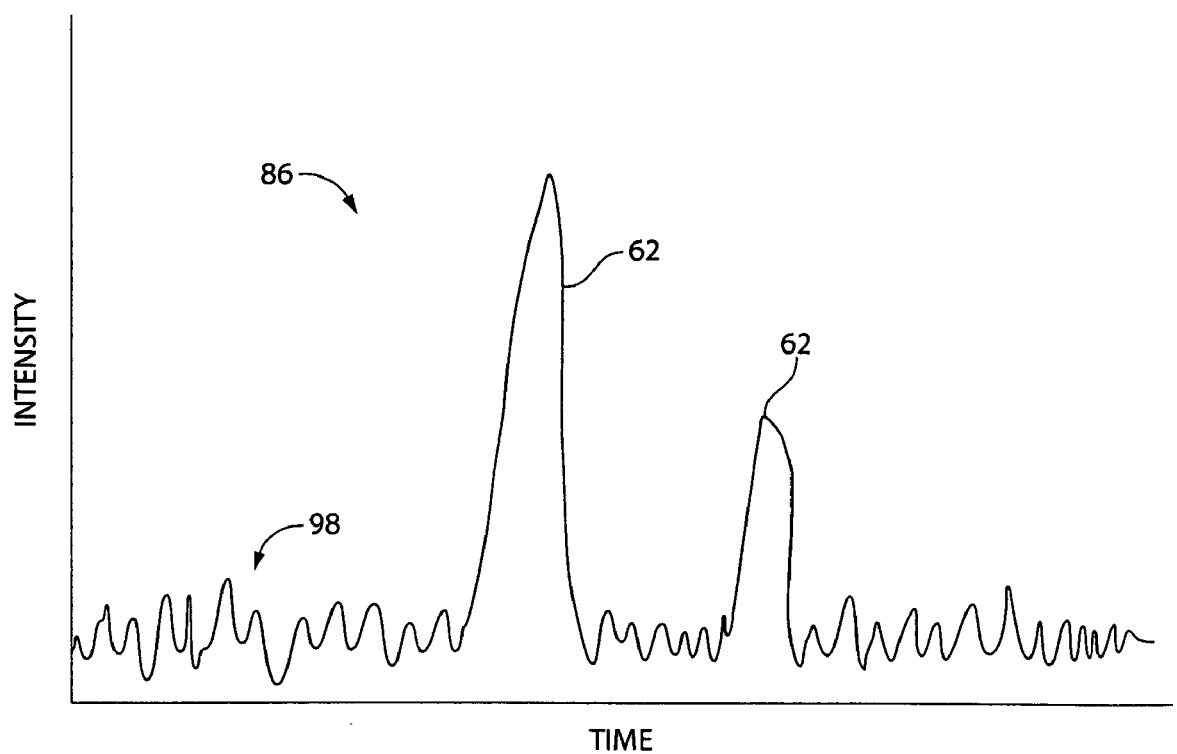
FIG. 16 shows a detection signal plotted on a graph of intensity versus time.

As previously discussed, illustrative embodiments of the invention are adapted to provide a first detection signal from a first detection zone 90 and a second detection signal from a second, smaller detection zone 92 that is overlapped with the first detection zone as shown by FIG. 15. The signals are passed to detectors, typically a point detector like an avalanche photodiode, which convert them into electrical signals of signal intensity versus time as represented by FIG. 16. As can be seen in FIG. 16, the peaks represent periods of high intensity, likely associated with a label being present within the detection zone.

The signal represented in FIG. 16 also displays a level of noise 98, varying in a stochastic manner with time. As previously discussed, the noise in the system may mask, or make the detection of emission signals more difficult. In some cases it may also cause an emission signal to be incorrectly identified. To address this, much of the noise is filtered out of the signals through filtering techniques previously discussed and as otherwise known to those of skill in the art. Additionally, in some embodiments, a threshold detection level is set such that any peaks below a particular intensity are ignored by the system.

As can be appreciated, a label passing through a circular detection zone along a diametral line, at a known speed, will produce an emission signal having a shape that may be anticipated in some illustrative embodiments. Additionally, in some embodiments, portions of the time varying signal may be analyzed to better understand whether a label is present and what type of label it might be. One analysis technique involves making a histogram of the peaks of a channel or channels over a given period of time, binned with respect to peak intensity, much like the histograms represented by FIGS. 13 and 14. As is to be appreciated, the distribution of peaks for a label passing along a diametral line of the detection zone should show a distribution somewhat like that of FIG. 13. Here, the highest intensity peaks associated with the label being in the most intense portion of the detection zone, typically the center, are few in number. The mid-level intensity points are the greatest in number and are generally associated with the label being disposed in central portions of the detection zone, but not the center most portion of the highest intensity. The lowest intensity portions of the histogram are associated with the label residing in the peripheral portions of the detection zone, which have the lowest intensity.

Figure 14:
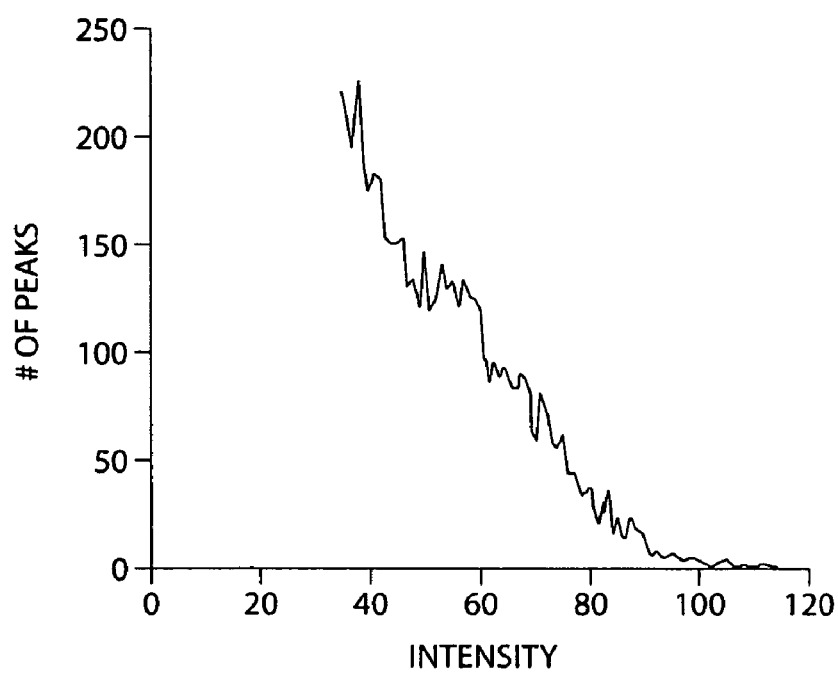
FIG. 14 shows a histogram of peak intensity associated with a first label passing through a central portion of a detection zone and a second label passing through a peripheral portion of a detection zone, according to an embodiment of the present invention.

As is to be appreciated, the presence of labels 94 on a second polymer 96 or of an unbound label within the detection zone may complicate the analysis of a first label 94 on a first polymer 96 within the zone. This may be the case particularly where the second label is in a peripheral portion of the detection zone. FIG. 14 shows a histogram of peaks sorted by intensity where the detection zone has a label passing along a substantially diametral line and a second label passing along a chord across a peripheral portion of the detection zone. FIG. 14 deviates from the expected histogram shown in FIG. 13 due to the additional, low intensity peaks that are contributed by the label passing through the peripheral portion of the detection zone.

Figure 17:
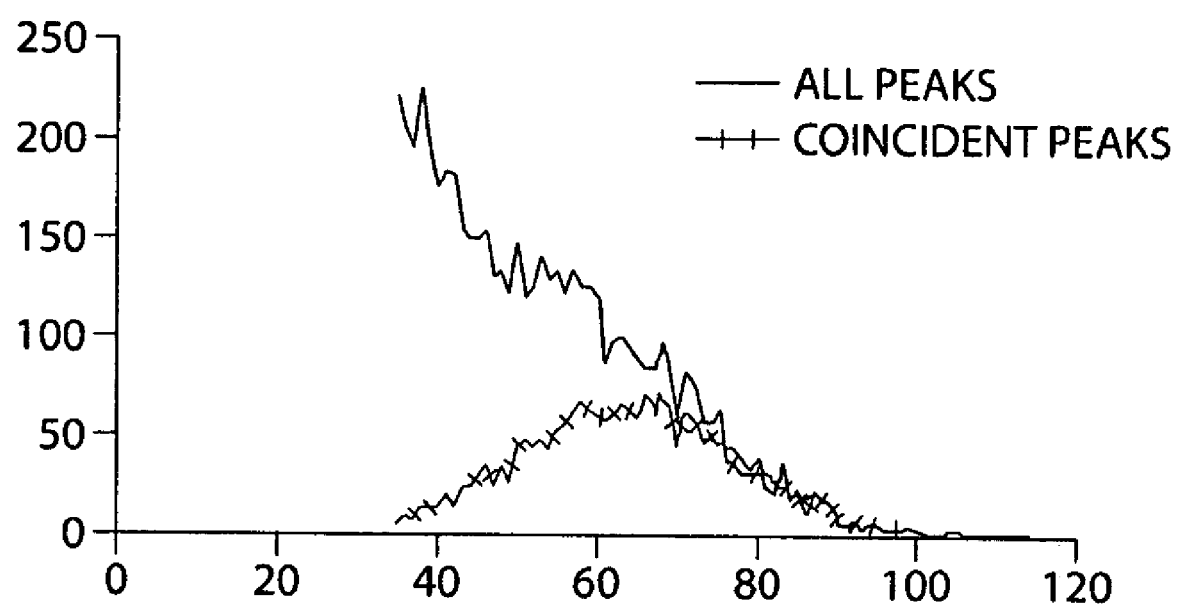
FIG. 17 shows an overlay of the histograms of both FIGS. 13 and 14.

In one illustrative embodiment of the invention, the contributions of the second label passing through the detection zone along a chord near the periphery are captured in a detection signal associated with a larger detection zone, but not a detection zone associated only with a smaller, central portion of the larger detection zone. FIG. 17 illustrates an overlay of histograms for peaks witnessed in the larger detection zone, and in the smaller detection zone. Here, coincident peaks are associated with labels passing through the common portions of both detection zones. In this regard, the portions of the detection signal associated with the second label passing along a peripheral portion of the larger detection zone may be identified and either separated or ignored, as desired.

The above described analysis may be used by embodiments of the detection system selectively at times when a second polymer is suspected of residing in a portion of the detection zone. In this regard, the data points that may be unclear to the system, or identifications of labels that are made with a lower degree of confidence, may be checked by the above described methods to verify the results and/or increase the level of confidence. In other illustrative embodiments, the detection signal from a larger detection zone may be continually used as a strategy to reduce the impact of noise within the detection system. In this manner, only peaks that are coincident between both detection zones may be reviewed for the presence or absence of labels. Thus, this scheme can be used to reduce the effects of systematic noise within the system, instead of or in addition to determining whether a portion of a signal is associated with a disturbance, such as a label of a second polymer lying within a peripheral portion of the detection zone.

Systems Using Wide Field Imaging Detectors

As illustrated above, many embodiments of the present invention accomplish sensitivity to individual labels within the detection zone with the assistance of confocal optics. In such systems, the entire contents of a detection zone may be excited using an excitation signal, such as a laser beam. A detection signal that emanates from the detection zone is processed by various optical signal processing instruments in a confocal microscope and is then transmitted to a detector where it is translated into an electrical signal for analysis by a data processor. Before the optical signal is passed to the detector, it is passed through a confocal aperture, which may remove out of focus light that might otherwise be introduced to the detector as noise. However, the confocal aperture also limits the view of the system to the focal point, or a subsection of the focal point.

It is also to be appreciated that some embodiments of detection systems illuminate an excitation zone that includes elements, other than labels, that react to the excitation signal. Some of these elements, such as carrier fluid that may surround a polymer in the sample area, may also alter any emission signal produced by contributing noise or other disturbance. For example, in some detection systems there are elements that lie within the excitation zone that may fluoresce, not unlike the labels that are bound to the polymer. Such fluorescence, although not typically as strong as that of the label, may act as noise in the detection signal. Also, the photons of the excitation signal, or even of the emission signals emanating from the labels, may cause Raman scattering throughout the carrier fluid that the polymer resides in. Raman scattering involves photons contacting molecules and bouncing off the molecules with energy at the same wavelength as the incident photon (elastic scattering) or with slightly less energy (inelastic scattering) than the incident photon and a corresponding different wavelength.

In an illustrative embodiment, polymers are provided to the detection zone where they are processed in a linear fashion. Only the polymers located within a relatively small detection zone, e.g., 1.00 micron in some embodiments, are detected and analyzed. This allows polymers to be passed through the detection zone in a relatively rapid manner and may result in relatively fast data processing. The processing speed may also be relatively fast due to the use of point detectors, which often process signals quicker than wide area detectors. Microfluidic devices may be used in detection systems to provide polymers to a detection zone in such a manner. Examples of such microfluidic devices are disclosed in U.S. patent application Ser. No. 10/821,664, filed on Apr. 19, 2004, which is hereby incorporated by reference in its entirety.

In other illustrative embodiments, a detection zone may be moved over, or scanned about a sample area. In this manner, the detection system can gather a larger image of the sample area by piecing together the image from all that was detected over the entire area. However, this may require the polymer to be stationary during the scanning process, which, in turn may increase the time it takes to perform an analysis.

Other approaches are available for imaging an entire sample area, or substantial portions thereof. In one illustrative embodiment, wide field imaging detectors may be used to image the entire sample area instead of scanning a single, confocal detection point about the sample area. CCD detectors or Complimentary Metal Oxide Semiconductor detectors (CMOS) are examples of detectors that may be used to accomplish this in some embodiments of the invention. Use of such wide field imaging devices allows a much larger portion of the sample area to be imaged at the same time. However, since such wide field imaging devices are typically taking in a greater amount of information representing a larger detection zone, they typically take longer to process an imaged signal. Nonetheless, they are still capable of detecting dynamic processes. In this regard, they can be used for dynamic detection of polymers passing through an entire sample area, or portions thereof.

CCDs and CMOS detectors are examples of wide-field imaging devices that may be used as detectors within embodiments of the present invention. A CCD is an array of photosensitive elements, where each element is capable of generating an electrical response to photons that are incident upon it. Each element may be referred to as a pixel and is typically a square having side dimensions between 20 and 30 microns. The pixels of the CCD collect photons that are incident upon them and convert them to electrical charges representative of the number of photons counted. The charges are then passed along a first direction of the two-dimensional array of pixels until all of the charges are represented in a single linear array of the CCD. After all of the counts are collected in this single array, they are passed into a corner of the two-dimensional array (i.e., an end of the linear array) where they may be passed, in turn, to the data processor. The data processor interprets the signal provided by the CCD and may reconstruct it as an array representing photon counts at each of the pixels over the entire area of the CCD. As may be appreciated, the processing time for a detection system that uses a CCD, or other type of wide field imaging device, may be substantially greater than a system that uses a point detector due to the additional, above-described processing steps. It is to be appreciated that although a CCD has been discussed as an exemplary wide field imaging device, other devices known to those in the art, such as CMOS detectors and others may also be used.

Using wide field imaging devices may require larger excitation zones 106 to be excited by an emitter. In many embodiments, this can be accomplished by passing an excitation beam, such as a laser beam or beams, through spherical lenses that spread the beam over a greater cross sectional area. However, other methods and devices can be used to illuminate larger portions of the sample area as will be appreciated by those of skill, as the present invention is not limited in this regard. In many embodiments, illuminating a larger portion of the sample area may cause an increase in noise contributions to detection signals. For example, it may introduce additional noise from Raman scattering, among other sources of noise. Although the confocal systems may also be subject to such noise, such systems may use a confocal aperture to reduce its effects. Most wide field detectors are not compatible with such confocal operations. As such, detection systems of the present invention may employ other methods to reduce contributions to the detection signal from areas outside of the focal plane.

Figure 18:
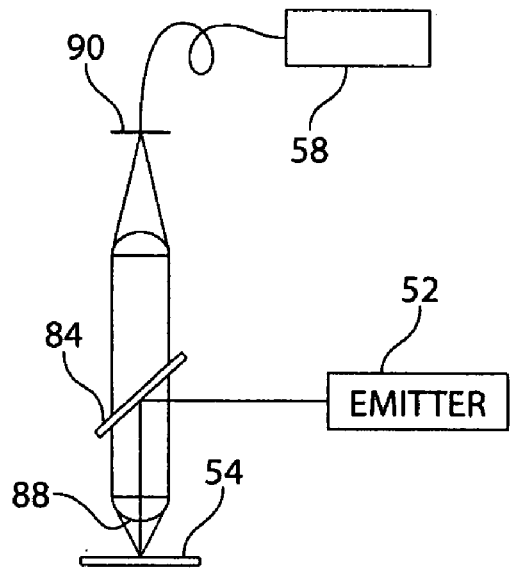
FIG. 18 shows schematic representations of detection systems using both point detectors and wide field imaging detectors.
Figure 18:
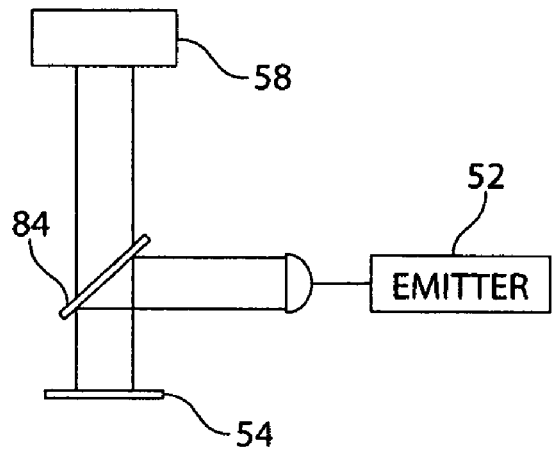

A schematic representation of both a point detection system and wide field imaging system are shown in FIG. 18. As can be seen, the detection zone of a wide field imaging system may be much larger than that of a point detection system. In the wide field imaging systems, a confocal aperture would need to be much larger to allow in focus light of the detection zone to pass to a detector. However, in many embodiments, using such a confocal aperture would only reduce a portion of the out of focus contribution. Such an aperture might not be able to reduce out of focus portions of the detection signal that are associated with portions of the sample area are lying in different vertical planes, both above and below the focal plane, which may be significantly greater than in systems using a point detector. As such, out of focus noise may be a problem to some embodiments of such detection systems.

To help reduce out of focus noise and prevent it from adversely affecting the ability of a detection system to detect emission signals, only portions of the sample area that lie within the in-focus portions of a sample area may be illuminated by the excitation signal. In this manner, very little, if any, out of focus elements are illuminated and thus these are prevented from contributing noise to the detection signal.

Figure 19:
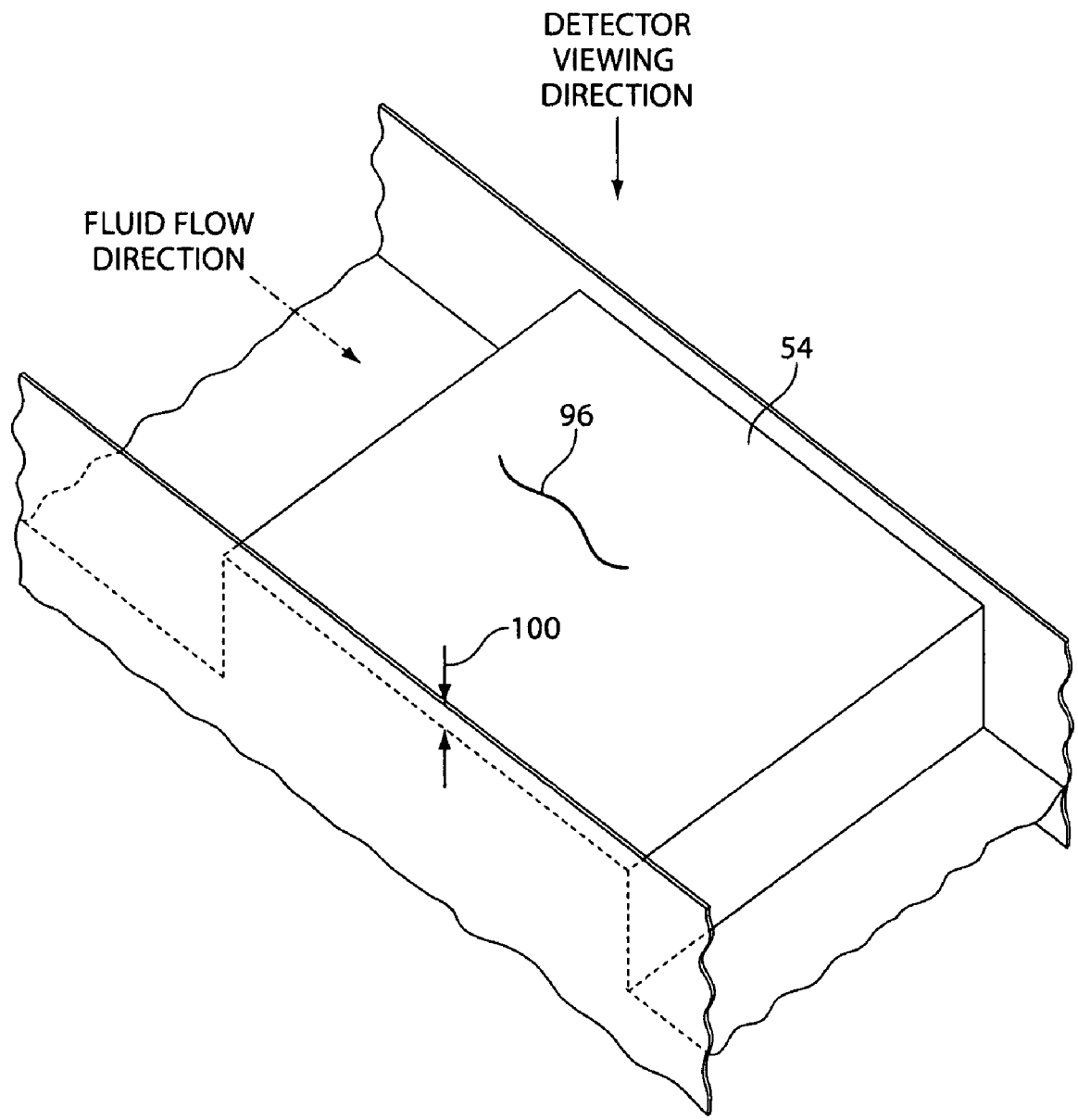
FIG. 19 shows a microchannel defining a thin sample area adapted to lie within the focal plane of a wide field imaging detector, according to one embodiment of the invention.

Various approaches can be used to limit illumination to the focal plane of the detection zone. In one illustrative embodiment, the sample area comprises a thin sheet of buffer solution 100 containing polymers and is surrounded by essentially noise free medium that will not react to an excitation signal. For example, the sample area may comprise a thin passage of a microfluidic channel, as represented by the channel shown in FIG. 19. The microfluidic channel may be defined by walls of glass formed of fused silica, which is a medium that produces little, if any, noise or emission signals when illuminated by an excitation signal. In one embodiment, the channel has a depth of 0.50 microns, a width of 50 microns, and a length of 50 microns. In another embodiment, the channel has a depth of 0.10 microns. Still, in another embodiment, the channel may have a depth of 0.080 microns or smaller. These channels may be manufactured through etching techniques or other processes known to those of skill, such as soft lithography and the like. In these embodiments, a carrier solution containing polymers flows through a microchannel and ultimately through the sample area. The entire microchannel is not required to have a thin cross sectional area like the sample area, but may transition to such a cross section, as shown in FIG. 19. Various other aspects of microfluidic systems, like those described in U.S. patent application Ser. No. 10/821,664, filed Apr. 19, 2004, which is hereby incorporated by reference in its entirety, may be employed by detection systems of the present invention.

Figure 20:
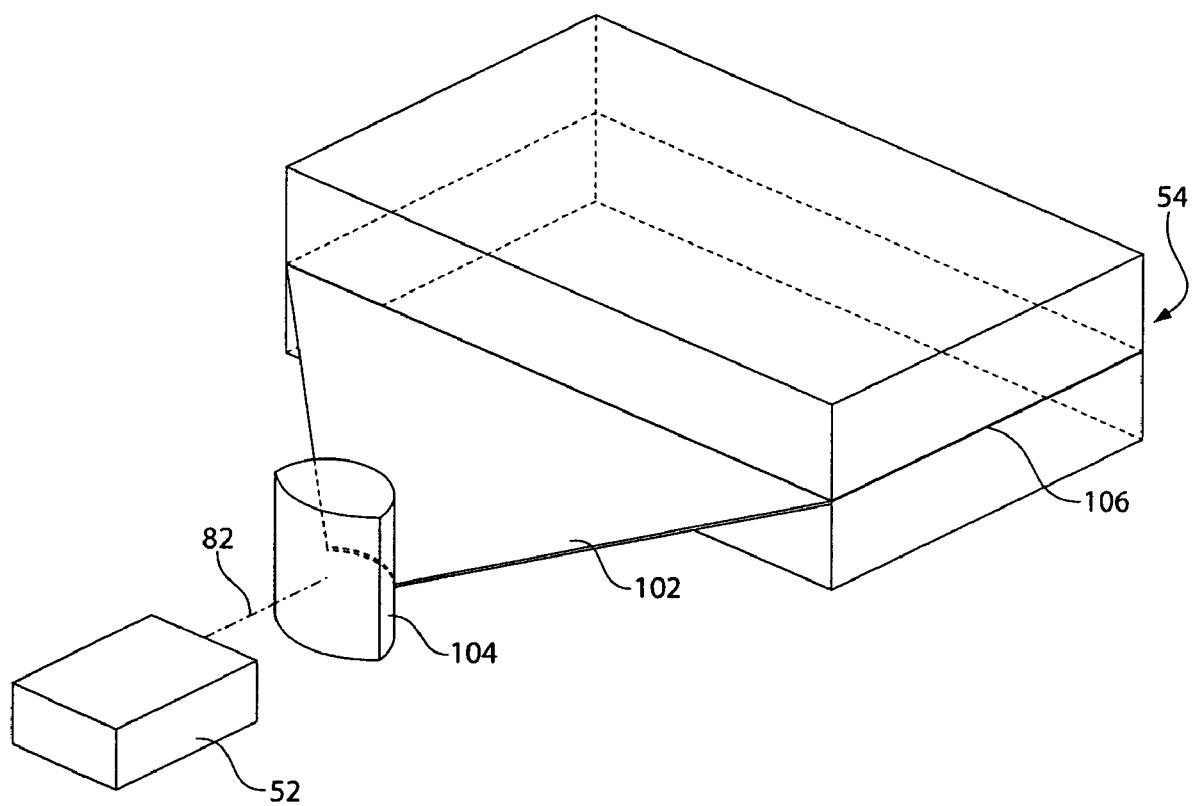
FIG. 20 shows a sample area being illuminated by a thin light sheet introduced into the sample area from a side direction.

In another illustrative embodiment, the sample area is only illuminated in the focal plane as the excitation signal is directed only to points within the focal plane. In one illustrative embodiment a sheet of light 102 may be projected into the sample area such that it lies substantially orthogonally to the detector entirely within the focal plane. Such a thin sheet of illumination may be formed through various methods. One such method includes directing an excitation signal, such as a coherent laser beam or collection of laser beams, through a cylindrical optical lens 104 that spreads the beam substantially in a single dimension. In such a system, the cylindrical lens may be positioned to direct the excitation signal, in the form of a thin sheet, into the sample area, such as a microfluidic channel, while the detector is positioned above the sample area. One such embodiment is shown in FIG. 20.

As can be appreciated, in embodiments where illumination by the excitation signal is limited to the focal plane, physical constraints about the polymer or the carrier fluid containing the polymer, like a thin microfluidic channel, are not required. However, many embodiments may couple some physical constraints with illumination of the sample area in this manner to help direct polymers into the illumination plane. Otherwise, in some embodiments, polymers pass by the detection zone without being illuminated.

As is to be appreciated, the above described embodiments of excitation signals may employ any of the previously described aspects of the detection system. For example, the excitation signal may comprise multiple lasers each adapted to excite a particular label used within the detection system. In one such embodiment, the lasers and labels described in Table 1 may be used, although others may be used in addition to, or in place of these as well. Also, the optical signal processing techniques for separating various emission signals of the detection signal may be combined with detection systems using wide field detectors, as the present invention is not limited in this regard. For instance, the system of polychroic and dichroic mirrors may be used to divide the detection signal into different channels, each associated with a particular portion of the electromagnetic spectrum.

As is to be appreciated, single point detectors, such as avalanche photodiodes or photomultipliers, may not be best suited to capture all of the information in a wide field image. As such, wide field imaging detectors 108, such as CCD's or CMOS detectors, may replace the single point detectors when such an approach is used. In one illustrative embodiment, a plurality of detectors used for each channel of a multi-channel detection system is replaced with a single, wide field imaging detector. As is to be appreciated, wide field imaging detectors are often more expensive than single point detectors. In this regard, it may be desirable to reduce the number of wide field detectors used in a system to also reduce the overall system cost. However, the wide field imaging detector, in many embodiments, should be capable of discerning different wavelengths of a detection signal in order to distinguish various emission signals contained within the detection system.

Figure 21:
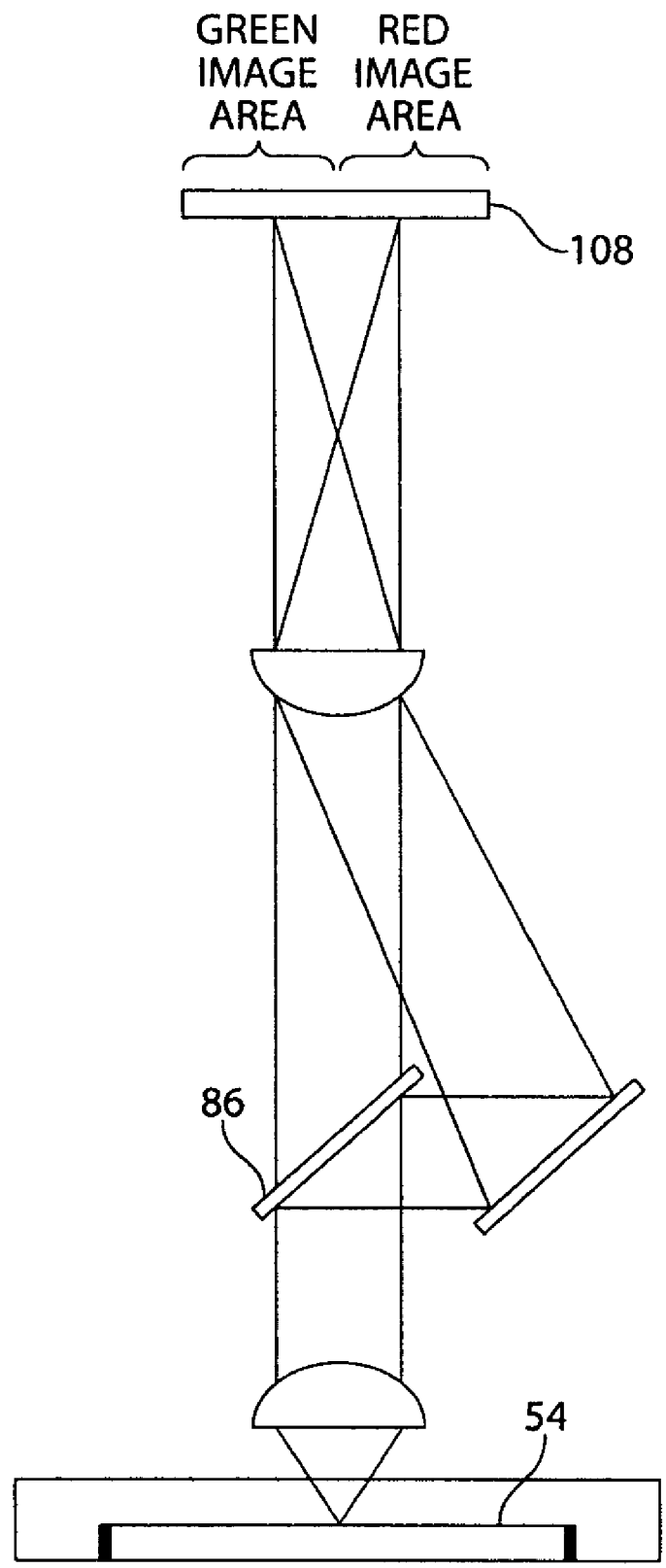
FIG. 21 shows spatial separation of emission signals in a wide field imaging system and projection of the separated signals onto separate portions of a wide field imaging detector.
Figure 22:
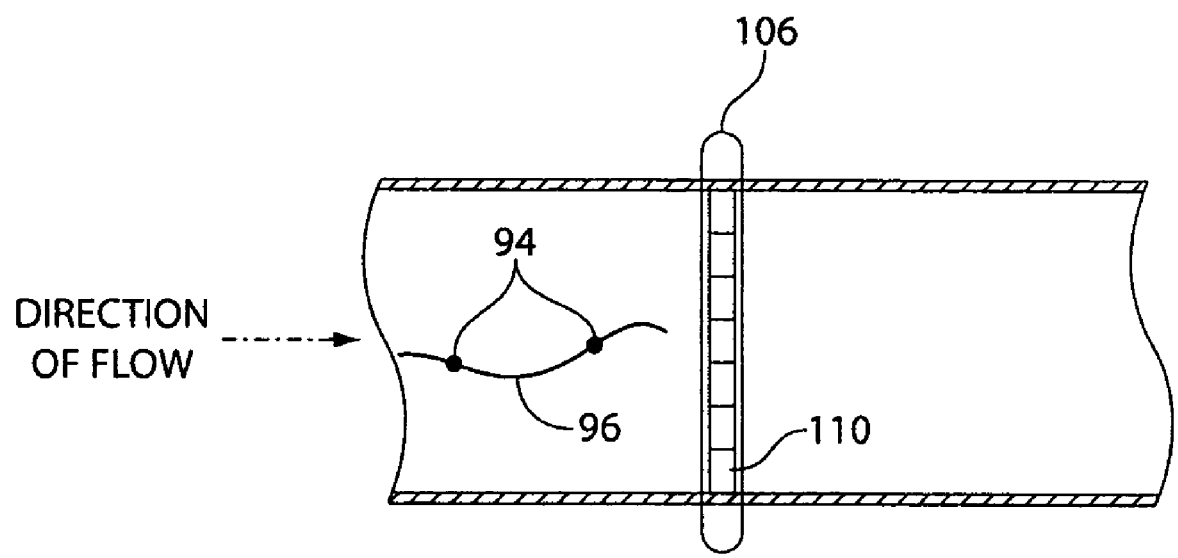
FIG. 22 shows a linear array detector and a corresponding detection zone disposed within a channel of a detection system.

In one illustrative embodiment, different portions of the detection signal associated with different portions of the electromagnetic spectrum are projected onto different spatial portions of the wide field imaging detector to allow them to be distinguished from one another. A system like that shown in FIG. 21 may accomplish this through the use of dichroic mirrors. FIG. 21 shows a wide field image being transmitted through a series of dichroic mirrors that divide the image based on the response curve of the given mirror, as previously discussed. In this manner, a first mirror may be used to extract an emission signal from the detection signal. In one embodiment, the detection signal is passed through a first dichroic mirror which removes a spectral band associated with an emission signal having the shortest wavelength (e.g., the blue label). The remaining portions of the detection signal are then transmitted to a second dichroic mirror which reflects the next larger wavelength band, which may be associated with another label (e.g., the green label). The process continues until all wavelength bands have been separated from the detection signal. As is to be appreciated, the manner in which the emission signals are separated from the detection signal may be performed according to other schemes, and other signal processing steps may be performed in between, before, or after separation steps, as the aforementioned process is merely exemplary for how emission signals may be separated from the detection signal.

As previously mentioned, after each of the separated emission signals, or similarly, the bands of wavelengths in which emission signals may be expected to reside, have been extracted from the detection signal, they are each directed onto a portion of a wide field imaging device as depicted in FIG. 21. Each band associated with a potential emission signal is projected onto the wide field imaging detector, such as a CCD, in a designated portion of the detector. The whole image detected by the CCD is converted to an electrical signal for subsequent data processing to understand whether a label is present and, if so, what type of label is present in the sample area at a given time. Although the signal transmitted by the CCD will suggest that various different polymers were present at different positions, corrections can be made during data processing to correct for the offset. In most embodiments, the offset is defined by the detection system setup; therefore correcting for the positions is made simpler as the valve remains constant for a system.

Linear Imaging Detector

As previously discussed, some detection systems use point detectors and confocal optics to detect emission signals, while others utilize a wide field imaging approach. There are benefits to each type of system. For example, point detection systems may collect detection and/or emission signals very rapidly, allowing for reduced assay time. Additionally, they can focus in on a small detection zone while filtering out noise from out of focus areas by passing the detection signal through a confocal aperture, or by using other noise reduction approaches. Although the point detection systems may be used, in some embodiments to collect data from a wide area, this may require scanning of the sample area, which may be difficult if polymers are passing through the sample area in a dynamic manner.

Wide field image detectors may capture a view of a much larger area in a single step. However, the rate at which images are collected and processed is typically slower than that of a single point detection system. The wide field imaging systems provide a larger target area to capture polymers that may be passing through the sample area. In this manner, it is easier to extend a detection zone across a greater portion of a sample area, if not all of the sample area. Here, the possibility of a polymer passing through a sample area undetected is reduced, if not eliminated, because the detection zone may be able to cover all potential locations where a polymer may reside. Additionally, although approaches may be taken to remove out of focus noise from the detection signal, these systems do not generally allow the use of a confocal aperture to remove out of focus noise from the detection signal as previously discussed.

Some embodiments of detection systems optimize between benefits of both point detection systems and wide field imaging systems by utilizing a detection zone that is extending in only one dimension. For example, in one illustrative embodiment, the detection zone extends in a linear array from one end of the sample area to the opposite end of the sample area. A linear CCD array 110 is one type of detector that may be used in this manner. A linear CCD array is constructed much like a two-dimensional CCD array and shares many of its characteristics; however, the linear CCD array has only a single row of photo receptors instead of a two-dimensional array of photo receptors. As such, the processing time associated with a linear CCD array is typically much faster than that of a two-dimensional CCD array, although it might not be as fast as that of a single point detector. As an example, some linear CCD arrays can read out data at the rate of 10,000 lines per second.

In one illustrative embodiment of the invention, a linear CCD array is extended across an entire path where polymers may be expected to pass. For instance, this arrangement may be used in embodiments of microfluidic detection systems. Here, the linear array may be used with an optical microscope to provide a detection zone that extends across a microfluidic channel in a direction substantially orthogonal to the flow of the carrier fluid in the system. In this manner, polymers residing within the carrier fluid will likely be detected as they pass through the detection zone. This may not be the case in embodiments using confocal microscopy where the detection zone is likely to be substantially smaller (e.g., it may be smaller than the distance across the sample area of the microfluidic channel).

Although systems using the linear CCD array may not lend themselves to use with a confocal aperture to reduce out of focus noise, such noise is less likely to be a problem in such systems. Since the linear CCD array may not require an excitation zone that is as large as a two-dimensional CCD array, not as much surrounding media will be excited. In this regard, there will be less material excited to contribute noise to the detection signal, thus reducing the need for a confocal aperture.

As described above, the excitation zone may be smaller than those of detection systems using a two-dimensional CCD array for other wide area imaging devices. For this reason, the excitation zone may be provided by a thin sheet of illumination, like that described above, which can be created using cylindrical lenses. This sheet of light may contain multiple, different lasers or a single laser, as the invention is not limited in this regard. In embodiments where multiple excitation signals are included within a single sheet of illumination, the above-described signal processing schemes may be used to separate emission signals from a detection signal that is received by the detection zone of the linear CCD array. Similarly, other schemes may be used as the invention is not limited in this respect.

Although embodiments using linear array detectors may not be amenable to the use of a confocal aperture to remove out of focus noise from the system, the same approaches discussed above with respect to removing noise from wide field imaging detection systems may be employed. For example, only the focal plane may be illuminated by the excitation signal(s) or the sample area may be contained to a very thin region with the surrounding features comprising essentially noise-free media. In this regard, noise may be dealt with adequately by embodiments using linear array detectors.

The methods of the invention can be used to generate unit specific information about a polymer by capturing polymer dependent impulses from the polymer using the devices described herein and elsewhere to manipulate the polymer. As used herein the term "unit specific information" refers to any structural information about one, some, or all of the units of the polymer. The structural information obtained by analyzing a polymer may include the identification of characteristic properties of the polymer which (in turn) allows, for example, for the identification of the presence of a polymer in a sample or a determination of the relatedness of polymers, identification of the size of the polymer, identification of the proximity or distance between two or more individual units of a polymer, identification of the order of two or more individual units within a polymer, and/or identification of the general composition of the units of the polymer. Since the structure and function of biological molecules are interdependent, the structural information can reveal important information about the function of the polymer. As used herein "analyzing a polymer" means obtaining information about the structure of the polymer, including but not limited to the information recited above.

A "polymer dependent impulse" as used herein is a detectable physical quantity which transmits or conveys information about the structural characteristics of a unit of a polymer. The physical quantity may be in any form which is capable of being detected. For instance the physical quantity may be electromagnetic radiation, chemical conductance, electrical conductance, etc. The polymer dependent impulse may arise from energy transfer, quenching, changes in conductance, radioactivity, mechanical changes, resistance changes, or any other physical changes.

The method used for detecting the polymer dependent impulse depends on the type of physical quantity generated. For instance if the physical quantity is electromagnetic radiation, then the polymer dependent impulse is optically detected. An "optically detectable" polymer dependent impulse as used herein is a light based signal in the form of electromagnetic radiation which can be detected by light detecting imaging systems. In some embodiments the intensity of this signal is measured. When the physical quantity is chemical conductance, then the polymer dependent impulse is chemically detected. A "chemically detected" polymer dependent impulse is a signal in the form of a change in chemical concentration or charge such as ion conductance which can be detected by standard means for measuring chemical conductance. If the physical quantity is an electrical signal, then the polymer dependent impulse is in the form of a change in resistance or capacitance. These types of signals and detection mechanisms are described in U.S. Pat. No. 6,355,420 B1.

The polymer dependent impulses may provide any type of structural information about the polymer. For instance these signals may provide the entire or portions of the entire sequence of the polymer (e.g., by the order of polymer dependent impulses).

A "polymer" as used herein is a compound having a linear backbone of individual units which are linked together by linkages. In some cases, the backbone of the polymer may be branched. Preferably the backbone is unbranched. The term "backbone" is given its usual meaning in the field of polymer chemistry. The polymers may be heterogeneous in unit and backbone composition. In one embodiment the polymers are, for example, nucleic acids, polypeptides, polysaccharides, or carbohydrates. In the most preferred embodiments, the polymer is a nucleic acid or a polypeptide. A polypeptide as used herein is a biopolymer comprised of linked amino acids.

The invention can be applied to various forms of nucleic acids including DNAs and RNAs. Examples of DNAs include genomic DNA, mitochondrial DNA or cDNA. In some important embodiments, the nucleic acid is not amplified in vitro prior to analysis. It may however be a nucleic acid that has been amplified in vivo (e.g., in a subject). Examples of RNAs include but are not limited to messenger RNA (mRNA), ribosomal RNA (rRNA), microRNA (mRNA), small interfering RNA (siRNA), and the like. MicroRNA is a class of noncoding RNAs generally about 22 nucleotides in size that are believed involved in the regulation of gene expression. siRNA is a double stranded RNA involved in RNA interference. It reportedly induces the formation of a ribonucleoprotein complex, which in turn mediates sequence-specific cleavage of a transcript target. It is to be understood that mRNA and siRNA can be used as either targets or as probes in the invention.

The term "nucleic acid" is used herein to mean multiple nucleotides (i.e., molecules comprising a sugar (e.g., ribose or deoxyribose) linked to an exchangeable organic base, which is either a substituted pyrimidine (e.g., cytosine (C), thymidine (T) or uracil (U)) or a substituted purine (e.g., adenine (A) or guanine (G)). "Nucleic acid" and "nucleic acid molecule" are used interchangeably, and used to refer to oligoribonucleotides as well as oligodeoxyribonucleotides. The terms shall also include polynucleosides (i.e., a polynucleotide minus a phosphate) and any other organic base containing polymer. Nucleic acids can be obtained from existing nucleic acid sources (e.g., genomic or cDNA), or by synthetic means (e.g., produced by nucleic acid synthesis). The nucleic acids can include substituted purines and pyrimidines such as C-propyne modified bases (Wagner et al., *Nature Biotechnology* 14:840-844, 1996). Purines and pyrimidines include but are not limited to adenine, cytosine, guanine, thymidine, 5-methylcytosine, 2-aminopurine, 2-amino-6-chloropurine, 2,6-diaminopurine, hypoxanthine, 2-thiouracil, pseudoisocytosine, and other naturally and non-naturally occurring nucleobases, substituted and unsubstituted aromatic moieties. Other such modifications are well known to those of skill in the art.

The nucleic acids may also encompass substitutions or modifications, such as in the bases and/or sugars. For example, they include nucleic acids having backbone sugars which are covalently attached to low molecular weight organic groups other than a hydroxyl group at the 3' position and other than a phosphate group at the 5' position. Thus, modified nucleic acids may include a 2'-O-alkylated ribose group. In addition, modified nucleic acids may include sugars such as arabinose instead of ribose. Thus the nucleic acids may be heterogeneous in backbone composition. In some embodiments, the nucleic acids are homogeneous in backbone composition.

As used herein with respect to linked units of a polymer, "linked" or "linkage" means two entities are bound to one another by any physicochemical means. Any linkage known to those of ordinary skill in the art, covalent or non-covalent, is embraced. Natural linkages, which are those ordinarily found in nature connecting the individual units of a particular polymer, are most common. Natural linkages include, for instance, amide, ester and thioester linkages. The individual units of a polymer analyzed by the methods of the invention may be linked, however, by synthetic or modified linkages. Polymers in which the units are linked by covalent bonds will be most common but may also include hydrogen bonded units are also embraced by the invention.

The polymer is made up of a plurality of individual units. An "individual unit" as used herein is a building block (e.g., a monomer) which can be linked directly or indirectly to other building blocks or monomers to form a polymer. The polymer preferably is a polymer of at least two different linked units. The at least two different linked units may produce or be labeled to produce different signals.

The "label" or "detectable moiety" may be, for example, light emitting, energy accepting, fluorescent, radioactive, or quenching as the invention is not limited in this respect. Many naturally occurring units of a polymer are light emitting compounds or quenchers, and thus are intrinsically labeled. Guidelines for selecting the appropriate labels, and methods for adding extrinsic labels to polymers are provided in more detail in U.S. Pat. No. 6,355,420 B1.

It is to be understood that a polymer that is said to "have" a label is a polymer that may have a label intrinsically as a part of the polymer. It is also to be understood that a polymer that is said to "have" a label may be a polymer that is bound to an extrinsic element that comprises the label, such as a fluorophor, a radio opaque marker, and the like.

Some detectable moieties can be detected directly by their ability to emit and/or absorb light of a particular wavelength. Other detectable moieties can be detected indirectly by their ability to bind, recruit and, in some cases, cleave another moiety which itself may emit or absorb light of a particular wavelength. An example of indirect detection is the use of a first enzyme label which cleaves a substrate into visible products. The label may be chemical, peptide or nucleic acid nature, although it is not so limited. Detectable moieties may be conjugated to a polymer using thiol, amino or carboxylic groups. Because it may be desirable to attach as many detectable labels to the polymer or to a polymer binding molecule (e.g., a unit specific marker or probe), such labels may be attached to amino or carboxylic groups which are common on proteins.

The detectable moieties described herein are referred to according to the systems by which they are detected. As an example, a fluorophore molecule is a molecule that can be detected using a system of detection that relies on fluorescence.

Generally, the detectable moiety can be selected from the group consisting of an electron spin resonance molecule (such as for example nitroxyl radicals), a fluorescent molecule, a chemiluminescent molecule, a radioisotope, an enzyme substrate, a biotin molecule, a streptavidin molecule, a peptide, an electrical charge transferring molecule, a semiconductor nanocrystal, a semiconductor nanoparticle, a colloid gold nanocrystal, a ligand, a microbead, a magnetic bead, a paramagnetic particle, a quantum dot, a chromogenic substrate, an affinity molecule, a protein, a peptide, nucleic acid, a carbohydrate, an antigen, a hapten, an antibody, an antibody fragment, and a lipid.

As used herein, the terms "charge transducing" and "charge transferring" are used interchangeably.

Examples of detectable labels include radioactive isotopes such as $P^{32}$ or $H^3$, epitope tags such as the FLAG or HA epitope, and enzyme tags such as alkaline phosphatase, horseradish peroxidase, β-galactosidase, etc. Other labels include chemiluminescent substrates, chromogenic substrates, fluorophores such as fluorescein (e.g., fluorescein succinimidyl ester), TRITC, rhodamine, tetramethyl-rhodamine, R-phycoerythrin, Cy-3, Cy-5, Cy-7, Texas Red, Phar-Red, allophycocyanin (APC), etc. Also envisioned by the invention is the use of semiconductor nanocrystals such as quantum dots, described in U.S. Pat. No. 6,207,392 as labels. Quantum dots are commercially available from Quantum Dot Corporation.

In some embodiments, the polymers are labeled with detectable moieties that emit distinguishable signals that can all be detected by one type of detection system. For example, the detectable moieties can all be fluorescent labels or radioactive labels. In other embodiments, the polymers are labeled with moieties that are detected using different detection systems. For example, one unit of a polymer may be labeled with a fluorophore while another may be labeled with radioactivity.

In one embodiment, analysis of the polymer involves detecting signals from the labels (potentially through the use of a secondary label, as the case may be), and determining the relative position of those labels relative to one another. In some instances, it may be desirable to further label the polymer with a standard marker that facilitates comparing the information so obtained with that from other polymers analyzed. For example, the standard marker may be a backbone label, or a label that binds to a particular sequence of nucleotides (be it a unique sequence or not), or a label that binds to a particular location in the nucleic acid molecule (e.g., an origin of replication, a transcriptional promoter, a centromere, etc.).

One subset of backbone labels for nucleic acids are nucleic acid stains that bind nucleic acids in a sequence independent manner. Examples include intercalating dyes such as phenanthridines and acridines (e.g., ethidium bromide, propidium iodide, hexidium iodide, dihydroethidium, ethidium homodimer-1 and -2, ethidium monoazide, and ACMA); minor grove binders such as indoles and imidazoles (e.g., Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine. All of the aforementioned nucleic acid stains are commercially available from suppliers such as Molecular Probes, Inc. Still other examples of nucleic acid stains include the following dyes from Molecular Probes: cyanine dyes such as SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red).

Polymers can be labeled using antibodies or antibody fragments and their corresponding antigen or hapten binding partners. Detection of such bound antibodies and proteins or peptides is accomplished by techniques well known to those ordinarily skilled in the art. Antibody/antigen complexes are easily detected by linking a label to the antibodies which recognize the polymer and then observing the site of the label. Alternatively, the antibodies can be visualized using secondary antibodies or fragments thereof that are specific for the primary antibody used. Polyclonal and monoclonal antibodies may be used. Antibody fragments include Fab, F(ab)$_2$, Fd and antibody fragments which include a CDR3 region.

The polymer may also be labeled with a unit specific marker such as a sequence specific probe or tag. "Sequence specific" when used in the context of a nucleic acid molecule means that the tag molecule recognizes a particular linear arrangement of nucleotides or derivatives thereof. An analogous definition applies to non-nucleic acid polymers. In preferred embodiments, the linear arrangement includes contiguous nucleotides or derivatives thereof that each bind to a corresponding complementary nucleotide on the target nucleic acid. In some embodiments, however, the sequence may not be contiguous as there may be one, two, or more nucleotides that do not have corresponding complementary residues on the target.

It is to be understood that any nucleic acid analog that is capable of recognizing a nucleic acid molecule with structural or sequence specificity can be used as a nucleic acid probe. In most instances, the nucleic acid probes will form at least a Watson-Crick bond with the nucleic acid molecule being analyzed (i.e., the target). In other instances, the nucleic acid probe can form a Hoogsteen bond with the target nucleic acid, thereby forming a triplex with the target nucleic acid. A nucleic acid sequence that binds by Hoogsteen binding enters the major groove of a target nucleic acid and hybridizes with the bases located there. Examples of these latter probes include molecules that recognize and bind to the minor and major grooves of nucleic acids (e.g., some forms of antibiotics). In preferred embodiments, the nucleic acid probes can form both Watson-Crick and Hoogsteen bonds with the target nucleic acid. BisPNA probes, for instance, are capable of both Watson-Crick and Hoogsteen binding to a target nucleic acid molecule. In some embodiments, probes with strong sequence specificity are preferred.

In some embodiments, the nucleic acid probe is comprised of a peptide nucleic acid (PNA), a bisPNA clamp, a pseudocomplementary PNA, a locked nucleic acid (LNA), DNA, RNA, or co-polymers of the above such as DNA-LNA co-polymers.

PNAs are DNA analogs having their phosphate backbone replaced with 2-aminoethyl glycine residues linked to nucleotide bases through glycine amino nitrogen and methylenecarbonyl linkers. PNAs can bind to both DNA and RNA targets by Watson-Crick base pairing, and in so doing form stronger hybrids than would be possible with DNA or RNA based tag probes.

Peptide nucleic acid is synthesized from monomers connected by a peptide bond (Nielsen, P. E. et al. *Peptide Nucleic Acids Protocols and Applications*, Norfolk: Horizon Scientific Press, p. 1-19 (1999)). It can be built with standard solid phase peptide synthesis technology.

PNA chemistry and synthesis allows for inclusion of amino acids and polypeptide sequences in the PNA design. For example, lysine residues can be used to introduce positive charges in the PNA backbone. All chemical approaches available for the modifications of amino acid side chains are directly applicable to PNAs. Several types of PNA designs exist, and these include single strand PNA (ssPNA), bisPNA, pseudocomplementary PNA (pcPNA).

The structure of PNA/DNA complex depends on the particular PNA and its sequence. Single stranded PNA (ssPNA) binds to ssDNA preferably in antiparallel orientation (i.e., with the N-terminus of the ssPNA aligned with the 3' terminus of the ssDNA) and with a Watson-Crick pairing. PNA also can bind to DNA with a Hoogsteen base pairing, and thereby forms triplexes with dsDNA (Wittung, P. et al., *Biochemistry* 36:7973 (1997)).

BisPNAs have multiple modes of binding to nucleic acids (Hansen, G. I. et al., *J. Mol. Biol.* 307(1):67-74 (2001)). One isomer includes two bisPNA molecules instead of one. It is formed at higher bisPNA concentration and has tendency to rearrange into the complex with a single bisPNA molecule.

Other isomers differ in positioning of the linker around the target DNA strands. All the identified isomers still bind to the same binding site/target.

Pseudocomplementary PNA (pcPNA) (Izvolsky, K. I. et al., *Biochemistry* 10908-10913 (2000)) also delivers two base pairs per every nucleotide of the target sequence. Hence, it can bind to short sequences similar to those that are bisPNA targets. The pcPNA strands are not connected by a hinge, and they have different sequences.

Hybridization of pcPNA can be less efficient than that of bisPNA because it needs three molecules to form the complex. However, the pseudocomplementary stands can be connected by a sufficiently long and flexible hinge.

Another bisPNA-based approach involves use of the displaced DNA strand (Demidov, V. V. et al., *Methods: A Companion to Methods in Enzymology* 23(2):123-131 (2001)). If the second bisPNA is hybridized close enough to the first one, then a run of DNA (up to 25 bp) is displaced, forming an extended P-loop. This run is long enough to be tagged. This combination is referred to as a PD-loop (Demidov, V. V. et al., *Methods: A Companion to Methods in Enzymology* 23(2):123-131 (2001)). Other applications for the opening are also designed including topological labels or "earrings". Tagging based on PD-loop has important advantages, including increased specificity.

Locked nucleic acid (LNA) molecules form hybrids with DNA, which are at least as stable as PNA/DNA hybrids (Braasch, D. A. et al., *Chem & Biol.* 8(1):1-7(2001)). Therefore, LNA can be used just as PNA molecules would be. LNA binding efficiency can be increased in some embodiments by adding positive charges to it. LNAs have been reported to have increased binding affinity inherently.

The probes can also be stabilized in part by the use of other backbone modifications. The invention intends to embrace the other backbone modifications such as but not limited to phosphorothioate linkages, phosphodiester modified nucleic acids, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof.

One limitation of the stability of nucleic acid hybrids is the length of the probe, with longer probes leading to greater stability than shorter probes. Notwithstanding this proviso, the probes of the invention can be any length ranging from at least 4 nucleotides long to in excess of 1000 nucleotides long. In preferred embodiments, the probes are 5-100 nucleotides in length, more preferably between 5-25 nucleotides in length, and even more preferably 5-12 nucleotides in length. The length of the probe can be any length of nucleotides between and including the ranges listed herein, as if each and every length was explicitly recited herein. It should be understood that not all residues of the probe need hybridize to complementary residues in the target nucleic acid. For example, the probe may be 50 residues in length, yet only 25 of those residues hybridize to the target nucleic acid. Preferably, the residues that hybridize are contiguous with each other.

The probes are preferably single stranded, but they are not so limited. For example, when the probe is a bisPNA it can adopt a secondary structure with the target nucleic acid resulting in a triple helix conformation, with one region of the bisPNA clamp forming Hoogsteen bonds with the backbone of the target molecule and another region of the bisPNA clamp forming Watson-Crick bonds with the nucleotide bases of the target molecule.

The specificity of nucleic acid probe binding to a target nucleic acid can be manipulated based on the hybridization conditions. For example, salt concentration and temperature can be modulated in order to vary the range of sequences recognized by the nucleic acid probes.

The polymers are analyzed using linear polymer analysis systems. A linear polymer analysis system is a system that analyzes polymers in a linear manner (i.e., starting at one location on the polymer and then proceeding linearly in either direction therefrom). As a polymer is analyzed, the detectable labels attached to it are detected in either a sequential or simultaneous manner. When detected simultaneously, the signals usually form an image of the polymer, from which distances between labels can be determined. When detected sequentially, the signals are viewed in histogram (signal intensity vs. time), that can then be translated into a map, with knowledge of the velocity of the polymer. It is to be understood that in some embodiments, the polymer is attached to a solid support, while in others it is free flowing. In either case, the velocity of the polymer as it moves past, for example, an interaction station or a detector, will aid in determining the position of the labels, relative to each other and relative to other detectable markers that may be present on the polymer.

Accordingly, the linear polymer analysis systems are able to deduce not only the total amount of label on a polymer, but perhaps more importantly in some embodiments, the location of such labels. The ability to locate and position the labels allows these patterns to be superimposed on other genetic maps, in order to orient and/or identify the regions of the genome being analyzed. In preferred embodiments, the linear polymer analysis systems are capable of analyzing nucleic acids individually (i.e., they are single molecule detection systems).

An example of such a system is the Gene Engine™ system described in PCT patent applications WO98/35012 and WO00/09757, published on Aug. 13, 1998, and Feb. 24, 2000, respectively, and in issued U.S. Pat. No. 6,355,420 B1, issued Mar. 12, 2002. The contents of these applications and patent, as well as those of other applications and patents, and references cited herein are incorporated by reference in their entirety. This system allows single nucleic acids to be passed through an interaction station in a linear manner, whereby nucleotides are interrogated individually in order to determine whether there is a detectable label conjugated to the nucleic acid molecule. Interrogation involves exposing the nucleic acid molecule to an energy source such as optical radiation of a set wavelength. In response to the energy source exposure, the detectable label on the nucleotide (if one is present) emits a detectable signal. The mechanism for signal emission and detection will depend on the type of label sought to be detected.

Other single molecule nucleic acid analytical methods which involve elongation of DNA molecule can also be used in the methods of the invention. These include optical mapping (Schwartz, D. C. et al., *Science* 262(5130):110-114 (1993); Meng, X. et al., *Nature Genet.* 9(4):432-438 (1995); Jing, J. et al., *Proc. Natl. Acad. Sci. USA* 95(14):8046-8051 (1998); and Aston, C. et al., *Trends Biotechnol.* 17(7):297-302 (1999)) and fiber-fluorescence in situ hybridization (fiber-FISH) (Bensimon, A. et al., *Science* 265(5181):2096-2098 (1997)). In optical mapping, nucleic acids are elongated in a fluid sample and fixed in the elongated conformation in a gel or on a surface. Restriction digestions are then performed on the elongated and fixed nucleic acids.

Ordered restriction maps are then generated by determining the size of the restriction fragments. In fiber-FISH, nucleic acids are elongated and fixed on a surface by molecular combing. Hybridization with fluorescently labeled probes allows determination of sequence landmarks on the nucleic acids. Both methods require fixation of elongated molecules so that molecular lengths and/or distances between probes can be measured. Pulse field gel electrophoresis can also be used to analyze the labeled nucleic acids. Pulse field gel electrophoresis is described by Schwartz, D. C. et al., *Cell* 37(1):67-75 (1984). Other nucleic acid analysis systems are described by Otobe, K. et al., *Nucleic Acids Res.* 29(22): E109 (2001), Bensimon, A. et al. in U.S. Pat. No. 6,248,537, issued Jun. 19, 2001, Herrick, J. et al., *Chromosome Res.* 7(6):409:423 (1999), Schwartz in U.S. Pat. No. 6,150,089 issued Nov. 21, 2000 and U.S. Pat. No. 6,294,136, issued Sep. 25, 2001. Other linear polymer analysis systems can also be used, and the invention is not intended to be limited to solely those listed herein.

The nature of such detection systems will depend upon the nature of the detectable moiety used to label the polymer. The detection system can be selected from any number of detection systems known in the art. These include an electron spin resonance (ESR) detection system, a charge coupled device (CCD) detection system, a fluorescent detection system, an electrical detection system, a photographic film detection system, a chemiluminescent detection system, an enzyme detection system, an atomic force microscopy (AFM) detection system, a scanning tunneling microscopy (STM) detection system, an optical detection system, a nuclear magnetic resonance (NMR) detection system, a near field detection system, and a total internal reflection (TIR) detection system, many of which are electromagnetic detection systems.

Optical detectable signals are generated, detected and stored in a database. The signals can be analyzed to determine structural information about the polymer. The signals can be analyzed by assessing the intensity of the signal to determine structural information about the polymer. The computer may be the same computer used to collect data about the polymers, or may be a separate computer dedicated to data analysis. A suitable computer system to implement embodiments of the present invention typically includes an output device which displays information to a user, a main unit connected to the output device and an input device which receives input from a user. The main unit generally includes a processor connected to a memory system via an interconnection mechanism. The input device and output device also are connected to the processor and memory system via the interconnection mechanism. Computer programs for data analysis of the detected signals are readily available from CCD (Charge Coupled Device) manufacturers.

Other interactions involved in methods of the invention will produce a nuclear radiation signal. As a radiolabel on a polymer passes through the defined region of detection, nuclear radiation is emitted, some of which will pass through the defined region of radiation detection. A detector of nuclear radiation is placed in proximity of the defined region of radiation detection to capture emitted radiation signals. Many methods of measuring nuclear radiation are known in the art including cloud and bubble chamber devices, constant current ion chambers, pulse counters, gas counters (i.e., Geiger-Müller counters), solid state detectors (surface barrier detectors, lithium-drifted detectors, intrinsic germanium detectors), scintillation counters, Cerenkov detectors, to name a few.

Other types of signals generated are well known in the art and have many detections means which are known to those of skill in the art. Some of these include opposing electrodes, magnetic resonance, and piezoelectric scanning tips. Opposing nanoelectrodes can function by measurement of capacitance changes. Two opposing electrodes create an area of energy storage, located effectively between the two electrodes. It is known that the capacitance of such a device changes when different materials are placed between the electrodes. This dielectric constant is a value associated with the amount of energy a particular material can store (i.e., its capacitance). Changes in the dielectric constant can be measured as a change in the voltage across the two electrodes. In the present example, different nucleotide bases or unit specific markers of a polymer may give rise to different dielectric constants. The capacitance changes as the dielectric constant of the unit specific marker of the polymer per the equation: $C=KC_o$, where K is the dielectric constant and $C_o$ is the capacitance in the absence of any bases. The voltage deflection of the nanoelectrodes is then outputted to a measuring device, recording changes in the signal with time.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A detection system for analyzing a polymer having three or more distinct fluorophores, each fluorophore having an excitation wavelength and a corresponding emission bandwidth, the detection system comprising:
   at least three different emitters that together create an excitation signal configured to excite each of the at least three fluorophores such that each fluorophore emits a distinct emission signal within its respective emission bandwidth and each distinct emission signal has an emission maximum separated by at least 60 nm from any other of the emission maximums;
   a polymer excitation zone that accepts the polymer, the polymer excitation zone being illuminated by the excitation signal of the at least three different emitters;
   a detector constructed and arranged to distinctly detect the emission signal from each of the at least three fluorophores; and
   a polychroic mirror adapted to prevent excitation signals emitted from the at least three different emitters from reaching the detector.

2. A detection system for analyzing a polymer having three or more distinct fluorophores, each fluorophore having an excitation wavelength and a corresponding emission bandwidth, the detection system comprising:

at least three different emitters that together create an excitation signal configured to excite each of the at least three fluorophores such that each fluorophore emits a distinct emission signal within its respective emission bandwidth that does not overlap any other of the distinct emission signals at normalized intensities above 70%;

a polymer excitation zone that accepts the polymer, the polymer excitation zone being illuminated by the excitation signal of the at least three different emitters;

a detector constructed and arranged to detect the distinct emission signal from each of the at least three fluorophores; and a polychroic mirror adapted to prevent excitation signals emitted from the at least three different emitters from reaching the detector.

3. The detection system of claim 2, wherein each of the emitters is constructed and arranged to emit a portion of the excitation signal within an excitation wavelength of one of the at least three distinct fluorophores such that each fluorophore emits a distinct emission signal within its respective emission bandwidth that does not overlap any other of the distinct emission signal at normalized intensities above 50%.

4. The detection system of claim 3, wherein each of the emitters is constructed and arranged to emit a portion of the excitation signal within an excitation wavelength of one of the at least three distinct fluorophores such that each fluorophore emits a distinct emission signal within its respective emission bandwidth that does not overlap any other of the distinct emission signal at normalized intensities above 30%.

5. A detection system for analyzing a polymer having three or more distinct fluorophores, each fluorophore having an excitation wavelength and a corresponding emission bandwidth, the detection system comprising:

at least three different emitters that together create an excitation signal having wavelengths configured to excite each of a corresponding one of the at least three fluorophores such that each fluorophore emits a distinct emission signal within its respective emission bandwidth, each of the at least three emitters and corresponding at least three fluorophores selected from a group consisting of: an emitter emitting an excitation wavelength of 488 nm and a corresponding fluorophore having an emission maximum substantially located at 512 nm, an emitter emitting an excitation a wavelength of 532 nm and a corresponding fluorophore having an emission maximum substantially located at 575 nm, an emitter emitting an excitation wavelength of 633 nm and a corresponding fluorophore having an emission maximum substantially located at 665 nm, and an emitter emitting an excitation wavelength of 750 nm and a corresponding fluorophore having an emission maximum substantially located at 775 nm or 806 nm;

a polymer excitation zone that accepts the polymer, the polymer excitation zone being illuminated by the excitation wavelengths of the at least three different emitters;

a detector constructed and arranged to detect the distinct emission signal from each of the at least three fluorophores; and a polychroic mirror adapted to prevent excitation signals emitted from the at least three different emitters from reaching the detector.

6. The detection system of claim 1, wherein the at least three fluorophores are selected from the group consisting of:
Bodipy FL fluorophore, Tamra fluorophore, Alexa 647 fluorophore, Alexa 750 fluorophore, and IR 38 fluorophore.

7. A method of detecting emissions of three or more distinct fluorophores bound to a polymer, the method comprising:

selecting three or more fluorophores, each of the fluorophores characterized by an excitation wavelength and a corresponding emission bandwidth, the emission bandwidth of each of the fluorophores not overlapping the emission bandwidth of any other of the fluorophores at normalized intensities above 70%;

attaching the three or more fluorophores to the polymer in a sequence specific manner;

illuminating each of the fluorophores with an excitation signal of multiple emitters, the excitation signal comprising excitation wavelengths of the corresponding fluorophores that cause each of the fluorophores to emit an emission signal within the emission bandwidth of the fluorophore;

removing the excitation signal from each of the emission signals with a polychroic filter; and detecting and analyzing the emission signal of each of the fluorophores.

8. A method for analyzing a polymer, the method comprising:

selecting at least three distinct fluorophores and an excitation signal emitted from at least three emitters, each of the at least three fluorophores having an excitation wavelength and a corresponding emission bandwidth, the excitation signal having excitation wavelengths that correspond to each of the at least three fluorophores such that each fluorophore emits a distinct emission signal having an emission maximum within its respective emission bandwidth, each of the at least three excitation wavelengths and corresponding at least three fluorophores selected from a group consisting of: an excitation wavelength of 488 nm and a corresponding fluorophore having an emission maximum substantially located at 512 nm, an excitation wavelength of 532 nm and a corresponding fluorophore having an emission maximum substantially located at 575 nm, an excitation wavelength of 633 nm and a corresponding fluorophore having an emission maximum substantially located at 665 nm, and an excitation wavelength of 750 nm and a corresponding fluorophore having an emission maximum substantially located at 775 nm or 806 nm;

binding the at least three fluorophores to a polymer in a sequence specific manner;

illuminating each of the fluorophores with the corresponding emitter at a common time;

removing the excitation signal from each of the emission signals with a polychroic filter; and detecting and analyzing the emission signal of each of the fluorophores for analysis.

9. The detection system of claim 1, wherein the detector comprises a plurality of detectors.

10. The detection system of claim 9, wherein the plurality of detectors comprises a plurality of avalanche photon detectors.

11. The detection system of claim 9, further comprising:
a plurality of dichroic mirrors constructed and arranged to direct each of the distinct emission signals into one of the plurality of detectors.

12. The detection system of claim 1, further comprising:
a bandpass filter for removing noise from each of the emission signals.

13. The detection system of claim 1, wherein the at least three different emitters comprise four different emitters and the at least three different fluorophores comprise four different fluorophores.

14. A detection system of claim 1, wherein the emitters comprise lasers.

15. A detection system of claim 1, wherein the excitation signals comprise coherent light.

16. The method of claim 7 wherein, selecting three or more fluorophores comprises selecting three or more fluorophores, each of the fluorophores characterized by an excitation bandwidth and a corresponding emission bandwidth, the emission bandwidth of each of the fluorophores not overlapping the emission bandwidth of any other of the fluorophores at normalized intensities above 50%.

17. The method of claim 16, wherein selecting three or more fluorophores comprises selecting three or more fluorophores, each of the fluorophores characterized by an excitation bandwidth and a corresponding emission bandwidth, the emission bandwidth of each of the fluorophores not overlapping the emission bandwidth of any other of the fluorophores at normalized intensities above 30%.

18. The method of claim 7, wherein selecting three or more fluorophores comprises selecting three or more different fluorophores from a group consisting of:

Bodipy FL fluorophore, Tamra fluorophore, Alexa 647 fluorophore, Alexa 750 fluorophore, and IR 38 fluorophore.

19. The method of claim 7, wherein selecting at least three distinct fluorophores and at least three emitters comprises selecting four fluorophores and four emitters.

20. The method of claim 7, wherein the polymer is a nucleic acid.

21. The method of claim 7, wherein detecting the emission signal from each of the fluorophores comprises:

separating each of the emission signals from one another with dichroic filters.

22. The method of claim 7, wherein detecting the emission signal from each of the fluorophores comprises:

passing the emission signal of some of the fluorophores through a bandpass filter.

23. The method of claim 7, wherein illuminating each of the fluorophores with the excitation signal comprises eliminating each of the fluorophores multiple lasers.

* * * * *